(12) United States Patent
Kim et al.

(10) Patent No.: US 6,699,689 B1
(45) Date of Patent: Mar. 2, 2004

(54) MASS PRODUCTION METHOD OF ANTIMICROBIAL PEPTIDE AND DNA CONSTRUCT AND EXPRESSION SYSTEM THEREOF

(75) Inventors: Jeong Hyun Kim, Taejon (KR); Min Hyung Kang, Taejon (KR); Jae Hyun Lee, Taejon (KR); Se Ho Park, Taejon (KR); Joo Won Lee, Taejon (KR); Seung Suh Hong, Taejon (KR); Hyun Soo Lee, Taejon (KR)

(73) Assignee: Samyang Genex Corporation, Chongno-ku (KR)

( * ) Notice: Subject to any disclaimer, the term of this patent is extended or adjusted under 35 U.S.C. 154(b) by 0 days.

(21) Appl. No.: 09/485,147

(22) PCT Filed: Jun. 8, 1999

(86) PCT No.: PCT/KR99/00282
§ 371 (c)(1),
(2), (4) Date: Apr. 25, 2000

(87) PCT Pub. No.: WO99/64611
PCT Pub. Date: Dec. 16, 1999

(30) Foreign Application Priority Data

Jun. 9, 1998 (KR) .......................................... 1998/22117
May 14, 1999 (KR) .......................................... 1998/17920

(51) Int. Cl.[7] .............................................. C12P 21/06
(52) U.S. Cl. ........................ 435/69.1; 435/183; 435/193; 435/252.3; 435/320.1; 536/23.2
(58) Field of Search ................................ 435/69.1, 183, 435/193, 252.3, 320.1; 536/23.2

(56) References Cited

U.S. PATENT DOCUMENTS

| | | | |
|---|---|---|---|
| 5,206,154 A | 4/1993 | Lai et al. | 435/69.7 |
| 5,593,866 A | 1/1997 | Hancock et al. | 435/69.7 |

OTHER PUBLICATIONS

J. Yun Tso et al., "Nucleotide Sequence of *Escherichia coli* purF and Deduced Amino Acid Sequence of Glutamine Phosphoribosylpyrophosphate", The Journal of Biological Chemistry, vol. 257 No. 7 pp. 3525–3531 (1982).

Christopher A. Makaroff, "Cloning of the *Bacillus subtilis* Glutamine Phosphoribosylpyrophosphate Amidotransferase Gene in *Escherichia coli*", The Journal of Biological Chemistry, vol. 258 No. 17 pp. 10586–10593 (1983).

J.H. Lee, et al., "Acidic Peptide–Mediated Expression of the Antimicrobial Peptide Buforin II as Tandem Repeats in *Escherichia Coli*", Protein Expr. Purif. Feb. 1998 (abstract).

L. Zhang et al., "Determinants of Recombinant Production of Antimicrobial Cationic Peptides and Creation of Peptide Variants in Bacteria", Biochem. Biophys. Res. Commun., Jun. 29, 1998, (abstract).

M. Okomoto et al., "Enhanced Expression of an Antimicrobial Peptide Sarcotoxin A by GUS Fusion in Transgenic Tobacco Plants", Plant Cell Physiol. Jan. 1998 (abstract).

C. Haught et al., "Recombinant Production and Purification of Novel Antisense Antimicrobial Peptide in *Escherichia Coli*", Biotechno. Bioeng. Jan. 1998 (abstract).

*Primary Examiner*—Ponnathapu Achutamurthy
*Assistant Examiner*—Christian L. Fronda
(74) *Attorney, Agent, or Firm*—Darby & Darby

(57) ABSTRACT

The present invention relates to DNA constructs that can produce antimicrobial materials efficiently from microorganisms and the preparation method thereof. The present invention also relates to the useful vector for the DNA construct. The DNA construct according to the present invention comprises a first gene coding for entire, a part of or a derivative of purF gene and a second gene coding for antimicrobial peptide. According to the present invention, antimicrobial peptides can be mass-produced by the following steps: preparing an expression vector containing a DNA construct comprising a first gene coding for an entire, a part of or a derivative of purF gene and a second gene coding for antimicrobial peptide; transforming the bacterial host cells with the above-mentioned vector, culturing the transformed cell to express the above-mentioned DNA construct; and recovering the above antimicrobial peptide.

8 Claims, 26 Drawing Sheets

APIDAECIN I (SEQ. ID NOS.: 41 and 42)

GGT AAC AAC CGT CCG GTT TAC ATC CCG CAG CCG CCG CAC CCG CGT ATC TGA
 G   N   N   R   P   V   Y   I   P   Q   P   P   H   P   R   I
EcoR I
GAATTC G

BOMBININ (SEQ. ID NOS.: 43 and 44)

GGT ATC GGT GCG CTG TCT GCG AAA GGT GCG CTG AAA GGT CTG GCG AAA GGT CTG GCG
 G   I   G   A   L   S   A   K   G   A   L   K   G   L   A   K   G   L   A
EcoR I
GAA CAC TTC GCG AAC TGA
 E   H   F   A   N

CPF I (SEQ. ID NOS.: 45 and 46)

GGT TTC GCG TCT TTC CTG GGT AAA GCG CTG AAA GCG GCG CTG AAA ATC
 G   F   A   S   F   L   G   K   A   L   K   A   A   L   K   I
                                                            EcoR I
GGT GCG AAC GCG CTG GGT GGT GCG CCG CAG CAG TGA GAATTC G
 G   A   N   A   L   G   G   A   P   Q   Q

FIG. 1A

DROSOCIN (SEQ. ID NOS.: 47 and 48)

GGT AAA CCG CGT CCG TAC TCT CCG CGT CCG ACC TCT CAC CCG CGT CCG ATC GCG GTT
 G   K   P   R   P   Y   S   P   R   P   T   S   H   P   R   P   I   A   V

TGA GAATTC G
    EcoR I

HNP-I (SEQ. ID NOS.: 49 and 50)

GCATGCC ATG GCG TGC TAC TGC CGT ATC CCG GCG TGC ATC GCG GGT GAG CGT CGT TAC
   NcoI      A   C   Y   C   R   I   P   A   C   I   A   G   E   R   R   Y

GGT ACC TGC ATC TAC CAG GGT CGT CTG TGG GCG TTC TGC TGC TGA GAATTC G
 G   T   C   I   Y   Q   G   R   L   W   A   F   C   C            EcoR I

INDOLICIDIN (SEQ. ID NOS.: 51 and 52)

C ATG ATC CTG CCG TGG AAA TGG CCG TGG TGG CCG TGG CGT TGA GAATTC C
   I   L   P   W   K   W   P   W   W   P   W   R                EcoR I

FIG. 1B

MELITTIN (SEQ. ID NOS.: 53 and 54)
GGT ATC GGT GCG GTT CTG AAA GTT CTG ACC ACC GGT CTG CCG GCG CTG ATC TCT TGG
 G   I   G   A   V   L   K   V   L   T   T   G   L   P   A   L   I   S   W
                                                                    EcoR I
ATC AAA CGT AAA CGT CAG CAG TGA GAATTC G
 I   K   R   K   R   Q   Q
MSI-344 (a) (SEQ. ID NOS.: 55 and 56)
        Nde I
TCCGGATCCAT ATG GGT ATC GGC AAA TTC CTG AAA AAG TAATGAAGGAGATATATTAATGC
            M   G   I   G   K   F   L   K   K        RBS
TTC GTT AAA ATC CTG AAA AAG GCT AAG AAA TTT GGT AAG AAA AAG TTC TTC GGA AAG GCG
 F   V   K   I   L   K   K   A   K   K   F   G   K   K   K   F   G   K   A
                                                             Ase I
MSI-344 (b) (SEQ. ID NOS.: 57 and 58)
         Sma I
GGATCCC GGG ATC GGC AAA TTC CTG AAA AAG GCT AAG AAA TTT GGT AAG GCG TTC GTT
         G   I   G   K   F   L   K   K   A   K   K   F   G   K   A   F   V

FIG. 1C

AAA ATC CTG AAA AAG TAATGAAGGAGATATATTAATGGATCC
K  I  L  K  K       RBS
                                    Ase I

PGQ (SEQ. ID NOS.: 59 and 60)

GGT GTT CTG TCT AAC GTT ATC GGT TAC CTG AAA AAA CTG GGT ACC GGT GCG
 G   V   L   S   N   V   I   G   Y   L   K   K   K   L   G   T   G   A

CTG AAC GCG GTT CTG AAA CAG TGA GAATTC G
 L   N   A   V   L   K   Q
                                    EcoR I

TACHYPLASIN I (SEQ ID NOS.: 61 and 62)

C ATG AAA TGG TGC TTC CGT GTT TGC TAC CGT GGT ATC TGC TAC CGT CGT TGC CGT TGA
   M   K   W   C   F   R   V   C   Y   R   G   I   C   Y   R   R   C   R

EcoR I
GAATTC G

XPF (SEQ. ID NOS.: 63 and 64)

GGT TGG GCG TCT AAA ATC GGT CAG ACC CTG GGT AAA ATC GCG AAA GTT GGT CTG AAA
 G   W   A   S   K   I   G   Q   T   L   G   K   I   A   K   V   G   L   K

FIG. 1D

EcoR I

GAA CTG ATC CAG CCG AAA TGA GAATTC G
 E   L   I   Q   P   K

BUFORIN I (SEQ. ID NOS.: 65 and 66)

GGC GCG GGA CGC GGC AAA CAA GGA GGC AAA GTG CGG GCT AAG GCC AAG ACC CGC TCA
 G   A   G   R   G   K   Q   G   G   K   V   R   A   K   A   K   T   R   S

TCC CGG GCA GGG CTC CAG TTC CCG GTC GGC CGT GTG CAC AGG CTC CTC CGC AAG GGC
 S   R   A   G   L   Q   F   P   V   G   R   V   H   R   L   L   R   K   G

AAC TAC TAA GGATCC
 N   Y
       BamIII

BUFORIN II (SEQ. ID NOS.: 67 and 68)

GGG ACC CGT TCC TCC CGT GCT GGT CTG CAG TTC CCG GTT GGT CGT GTT CAC CGT CTG
 G   T   R   S   S   R   A   G   L   Q   F   P   V   G   R   V   H   R   L

CTG CGT AAA TAA TGA AGG AGA TAT ATT AAT GGATCC
 L   R   K
                             BamIII

FIG. 1E

BUFORIN II a (SEQ. ID NOS.: 69 and 70)

GGG CGT GCT GGT CTG CAG TTC CCG GTT GGT CGT GTT CAC CGT CTG CTG CGT AAA TAA
 G   R   A   G   L   Q   F   P   V   G   R   V   H   R   L   L   R   K

TGA AGG AGA TAT ATT AAT GGATCC
                        BamHI

BUFORIN II b (SEQ. ID NOS.: 71 and 72)

GGG CGT GCT GGT CTG CAG TTC CCG GTT GGT CGC CTG CTG CGC CGT CTG CTG CGT CGC
 G   R   A   G   L   Q   F   P   V   G   R   L   L   R   R   L   L   R   R

CTG CTG CGC TAA TGA AGG AGA TAT ATT AAT GGATCC
 L   L   R                              BamHI

FIG. 1F

F    (SEQ. ID NOS.: 73 and 74)

NdeI

1  CATATGTGCGGTATTGTCGGTATCGCCGGTGTTATGCCGGTTAACCAGTC
      M  C  G  I  V  G  I  A  G  V  M  P  V  N  Q  S

51  GATTTATGATGCCTTAACGGTGCTTCAGCATCGCGGTCAGGATGCCGCCG
    I  Y  D  A  L  T  V  L  Q  H  R  G  Q  D  A  A

101  GCATCATCACCATAGATGCCAATAACTGCTTCCGTTTGCGTAAAGCGAAC
     G  I  I  T  I  D  A  N  N  C  F  R  L  R  K  A  N
                                          NdeI

151  GGGCTGGTGAGCGATGTATTTGAAGCTCGCCATATG
     G  L  V  S  D  V  F  E  A  R  H  M

F'   (SEQ. ID NOS.: 75 and 76)

NdeI

1  CATATGTGCGGTATTGTCGGTATCGCCGGTGTTATGCCGGTTAACCAGTC
      M  C  G  I  V  G  I  A  G  V  M  P  V  N  Q  S

51  GATTTATGATGCCTTAACGGTGCTTCAGCATCGCGGTCAGGATGCCGCCG
    I  Y  D  A  L  T  V  L  Q  H  R  G  Q  D  A  A

101  GCATCATCACCATAGATGCCAATAACTGCTTCCGTTTGCGTAAAGCGAAC
     G  I  I  T  I  D  A  N  N  C  F  R  L  R  K  A  N
                                          SspI

151  GCGCTGGTGAGCGATGTATTTGAAGCTAATATT
     A  L  V  S  D  V  F  E  A  N

F3 (HA)   (SEQ. ID NOS.: 77 and 78)

NdeI

1  CATATGTGCGGTATTGTCGGTATCGCCGGTGTTATGCCGGTTAACCAGTC
      M  C  G  I  V  G  I  A  G  V  M  P  V  N  Q  S

51  GATTTATGATGCCTTAACGGTGCTTCAGCATCGCGGTCAGGATGCCGCCG

A — — — — — — — — — — — — — — — — — — — — — A
```
         I  Y  D  A  L  T  V  L  Q  H  R  G  Q  D  A  A
101 GCATCATCACCATAGATGCCAATAACTGCTTCCGTTTGCGTAAAGCGAAC
     G  I  I  T  I  D  A  N  N  C  F  R  L  R  K  A  N
                                              SspI
151 GCGCTGGTGAGCGATGTATTTGAAGCTGCGCATGCGAATATT
     A  L  V  S  D  V  F  E  A  A  H  A  N
```

F3 (CB) (SEQ. ID NOS.: 79 and 80)

AS SAME AS 1-100 F3(HA)

```
                                  BspLU11 I
151 GCGCTGGTGAGCGATGTATTTGAAGCTCGCCACATGTGGATCCCG
     A  L  V  S  D  V  F  E  A  R  H  M
```

F4 (HA) (SEQ. ID NOS.: 81 and 82)

```
    NdeI
  1 CATATGTGCGGTATTGTCGGTATCGCCGGTGTTATGCCGGTTAACCAGTC
         M  C  G  I  V  G  I  A  G  V  M  P  V  N  Q  S
 51 GATTTATGATGCCTTAACGGTGCTTCAGCATCGCGGTCAGGATGCCGCCG
     I  Y  D  A  L  T  V  L  Q  H  R  G  Q  D  A  A
101 GCATCATCACCATAGATGCCAATAACTGCTTCCGTTTGCGTAAAGCGAAC
     G  I  I  T  I  D  A  N  N  C  F  R  L  R  K  A  N
                                              NdeI
151 GGGCTGGTGAGCGATGTATTTGAAGCTCGCCATATGCAGCGTTTGCAGGG
      G  L  V  S  D  V  F  E  A  R  H  M  Q  R  L  Q  G
201 CAATATGGGCATTGGTCATGTGCGTTACCCCACGGCTGGCAGCTCCAGCG
     N  M  G  I  G  H  V  R  Y  P  T  A  G  S  S  S
251 CCTCTGAAGCGCAGCCGTTTTACGTTAACTCCCCGTATGGCATTACGCTT
     A  S  E  A  Q  P  F  Y  V  N  S  P  Y  G  I  T  L
```

```
301 GCCCACATCGGCAATCTGACCAACGCTCACGAGTTGCGTAAAAAACTGTT
     A   H   I   G   N   L   T   N   A   H   E   L   R   K   K   L   F
351 TGAAGAAAAACGCCGCCACATCAACACCACTTCCGACTCGGAAATTCTGC
       E   E   K   R   R   H   I   N   T   T   S   D   S   E   I   L
401 TTAATATCTTCGCCAGCGAGCTGGACAACTTCCGCCACTACCCGCTGGAA
     L   N   I   F   A   S   E   L   D   N   F   R   H   Y   P   L   E
              SspI
451 GCCGACAATATT
     A   D   N
```

F4a (HA)   (SEQ. ID NOS.: 83 and 84)

AS SAME AS 1-150 F4(HA)

```
151 GCGCTGGTGAGCGATGTATTTGAAGCTCGCCATATGCAGCGTTTGCAGGG
     A   L   V   S   D   V   F   E   A   R   H   M   Q   R   L   Q   G
```

AS SAME AS 201-462 F4 (HA)

F4a (CB)   (SEQ. ID NOS.: 85 and 86)

AS SAME AS 1-450 F4 (HA)

```
         BspLU11 I
451 GCCGACATGTGG
     A   D   M
```

F5 (SEQ. ID NOS.: 87 and 88)

```
     NdeI
  1 CATATGCAGCGTTTGCAGGGCAATATGGGCATTGGTCATGTGCGTTACCC
     M   Q   R   L   Q   G   N   M   G   I   G   H   V   R   Y   P
 51 CACGGCTGGCAGCTCCAGCGCCTCTGAAGCGCAGCCGTTTTACGTTAACT
       T   A   G   S   S   S   A   S   E   A   Q   P   F   Y   V   N
101 CCCCGTATGGCATTACGCTTGCCCACATCGGCAATCTGACCAACGCTCAC
```

```
         S   P   Y   G   I   T   L   A   H   I   G   N   L   T   N   A   H
     151 GAGTTGCGTAAAAAACTGTTTGAAGAAAAACGCCGCCACATCAACACCAC
           E   L   R   K   K   L   F   E   E   K   R   R   H   I   N   T   T
     201 TTCCGACTCGGAAATTCTGCTTAATATCTTCGCCAGCGAGCTGGACAACT
             S   D   S   E   I   L   L   N   I   F   A   S   E   L   D   N
                                            SspI
     251 TCCGCCACTACCCGCTGGAAGCCCACAATATT
             F   R   H   Y   P   L   E   A   D   N
     BF (SEQ. ID NOS.: 89 and 90)
        NdeI
      1 CATATGCTTGCTGAAATCAAAGGCTTAAATGAAGAATGCGGCGTTTTTGG
              M   L   A   E   I   K   G   L   N   E   E   C   G   V   F   G
     51 GATTTGGGGACATGAAGAAGCCCCGCAAATCACGTATTACGGTCTCCACA
              I   W   G   H   E   E   A   P   Q   I   T   Y   Y   G   L   H
                                                           SspI
    101 GCCTTCAGCACCGAGGACAGGAGGGTGCTGGCAATATT
             S   L   Q   H   R   G   Q   E   G   A   G   N
```

FIG. 2D

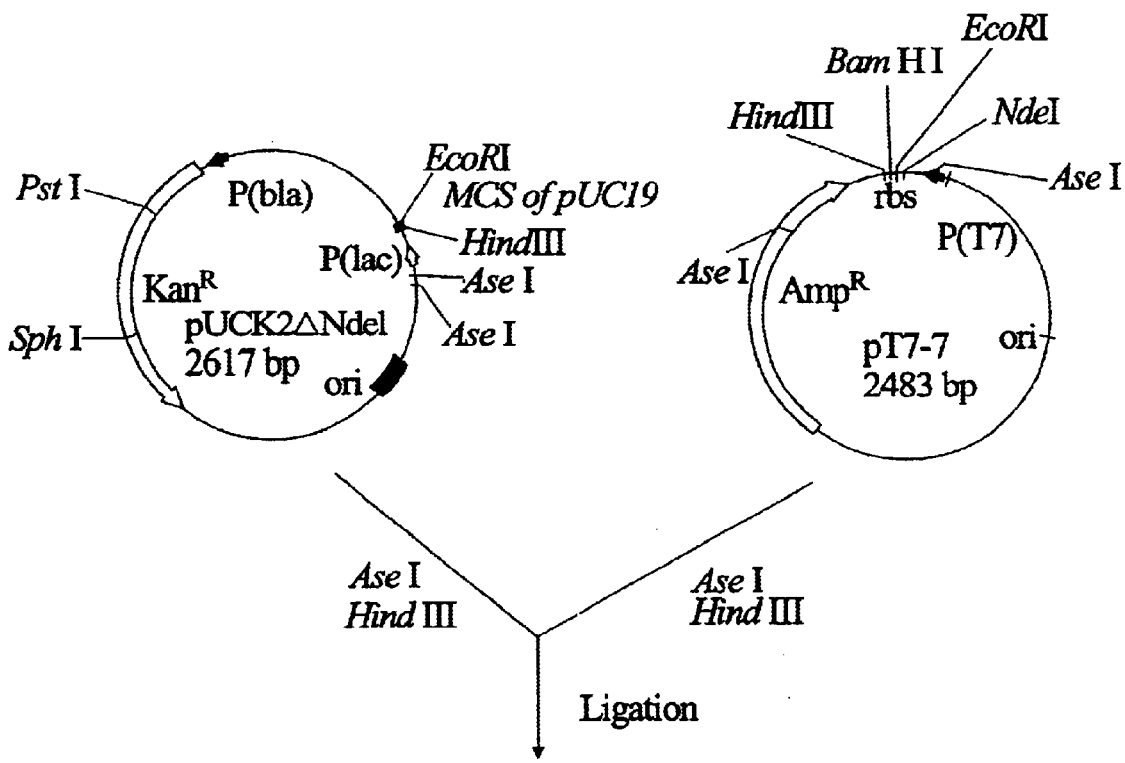
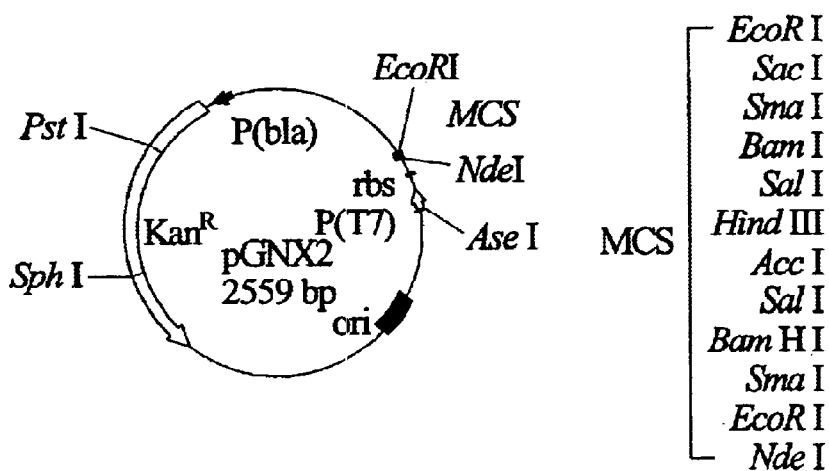
FIG. 6B

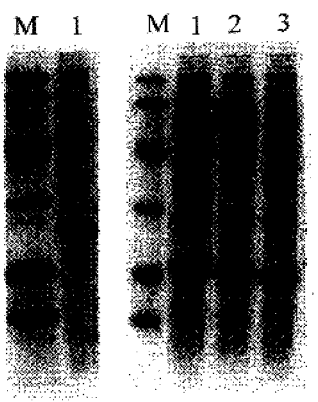
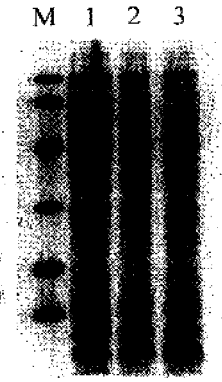
FIG. 14(A)  FIG. 14(B)  FIG. 14(C)  FIG. 14(D)

SEQUENCE LISTING

<160> NUMBER OF SEQ ID NOS: 93

<210> SEQ ID NO 1
<211> LENGTH: 32
<212> TYPE: DNA
<213> ORGANISM: Artificial Sequence
<220> FEATURE:
<223> OTHER INFORMATION: primer for the synthesis of MSI-344 (32mer)

<400> SEQUENCE: 1
tccggatcca tatgggtatc ggcaaattcc tg                          32

<210> SEQ ID NO 2
<211> LENGTH: 42
<212> TYPE: DNA
<213> ORGANISM: Artificial Sequence
<220> FEATURE:
<223> OTHER INFORMATION: primer for the synthesis of MSI-344 (42mer)

<400> SEQUENCE: 2
gcattaatat atctccttca ttactttttc aggattttaa cg               42

<210> SEQ ID NO 3
<211> LENGTH: 32
<212> TYPE: DNA
<213> ORGANISM: Artificial Sequence
<220> FEATURE:
<223> OTHER INFORMATION: primer for the synthesis of MSI-344 (32mer)

<400> SEQUENCE: 3
ggatcccggg atcggcaaat tcctgaaaaa gg                          32

<210> SEQ ID NO 4
<211> LENGTH: 28
<212> TYPE: DNA
<213> ORGANISM: Artificial Sequence
<220> FEATURE:
<223> OTHER INFORMATION: primer for the synthesis of MSI-344 (28mer)

<400> SEQUENCE: 4
ggatccatta atatatctcc ttcattac                               28

<210> SEQ ID NO 5
<211> LENGTH: 57
<212> TYPE: DNA
<213> ORGANISM: Artificial Sequence
<220> FEATURE:
<223> OTHER INFORMATION: primer for the synthesis of Apidaecin (57mer)

<400> SEQUENCE: 5
ggtaacaacc gtccggttta catcccgcag ccgcgtccgc cgcacccgcg tacttga    57

<210> SEQ ID NO 6
<211> LENGTH: 62
<212> TYPE: DNA
<213> ORGANISM: Artificial Sequence
<220> FEATURE:
<223> OTHER INFORMATION: primer for the synthesis of Apidaecin (62mer)

<400> SEQUENCE: 6
aattctcaag tacgcgggtg cggcggacgc ggctgcggga tgtaaaccgg acggttgtta    60
cc                                                                  62

<210> SEQ ID NO 7
<211> LENGTH: 48
<212> TYPE: DNA
<213> ORGANISM: Artificial Sequence
<220> FEATURE:
<223> OTHER INFORMATION: primer for the synthesis of Bombinin (48mer)

<400> SEQUENCE: 7
ggtatcggtg cgctgtctgc gaaaggtgcg ctgaaaggtc tggcgaaa         48

<210> SEQ ID NO 8
<211> LENGTH: 58
<212> TYPE: DNA
<213> ORGANISM: Artificial Sequence
<220> FEATURE:
<223> OTHER INFORMATION: primer for the synthesis of Bombinin (58 mer)

<400> SEQUENCE: 8
cgaattctca gttcgcgaag tgttgcgcca gacctttcgc agacctttc agcgcacc    58

<210> SEQ ID NO 9
<211> LENGTH: 48
<212> TYPE: DNA
<213> ORGANISM: Artificial Sequence
<220> FEATURE:
<223> OTHER INFORMATION: primer for the synthesis of CPF (48mer)

<400> SEQUENCE: 9
ggtttcgcgt ctttcctggg taaagcgctg aaagcggcgc tgaaaatc          48

<210> SEQ ID NO 10
<211> LENGTH: 60
<212> TYPE: DNA
<213> ORGANISM: Artificial Sequence
<220> FEATURE:
<223> OTHER INFORMATION: primer for the synthesis of CPF (60mer)

<400> SEQUENCE: 10
cgaattctca ctgctgcggc gcaccaccca gcgcgttcgc accgattttc agcgccgctt    60
                                                                    60

<210> SEQ ID NO 11
<211> LENGTH: 39
<212> TYPE: DNA
<213> ORGANISM: Artificial Sequence
<220> FEATURE:
<223> OTHER INFORMATION: primer for the synthesis of Drosocin (39mer)

<400> SEQUENCE: 11
ggtaaaccgc gtccgtactc tccgcgtccg acctctcac          39

<210> SEQ ID NO 12
<211> LENGTH: 49
<212> TYPE: DNA
<213> ORGANISM: Artificial Sequence
<220> FEATURE:
<223> OTHER INFORMATION: primer for the synthesis of Drosocin (49mer)

<400> SEQUENCE: 12
cgaattctca aaccgcgatc ggacgcgggt gagaggtcgg acgcggaga         49

<210> SEQ ID NO 13
<211> LENGTH: 60
<212> TYPE: DNA
<213> ORGANISM: Artificial Sequence
<220> FEATURE:
<223> OTHER INFORMATION: primer for the synthesis of HNP-1 (60mer)

-continued

```
<400> SEQUENCE: 13
gcatgccatg gcgtgctact gccgtatccc ggcgtgcatc gcgggtgaac gtcgttacgg      60
                                                                     60

<210> SEQ ID NO 14
<211> LENGTH: 60
<212> TYPE: DNA
<213> ORGANISM: Artificial Sequence
<220> FEATURE:
<223> OTHER INFORMATION: primer for the synthesis of HNP-1 (60mer)

<400> SEQUENCE: 14
cgaattctca gcagcagaac gcccacagac gaccctggta gatgcaggta ccgtaacgac      60
                                                                     60

<210> SEQ ID NO 15
<211> LENGTH: 47
<212> TYPE: DNA
<213> ORGANISM: Artificial Sequence
<220> FEATURE:
<223> OTHER INFORMATION: primer for the synthesis of Indolicidin (47mer)

<400> SEQUENCE: 15
catgatcctg ccgtggaaat ggccgtggtg gccgtggcgt cgttgag                    47

<210> SEQ ID NO 16
<211> LENGTH: 47
<212> TYPE: DNA
<213> ORGANISM: Artificial Sequence
<220> FEATURE:
<223> OTHER INFORMATION: primer for the synthesis of Indolicidin (47mer)

<400> SEQUENCE: 16
aattctcaac gacgccacgg ccaccacggc catttccacg gcaggat                    47

<210> SEQ ID NO 17
<211> LENGTH: 48
<212> TYPE: DNA
<213> ORGANISM: Artificial Sequence
<220> FEATURE:
<223> OTHER INFORMATION: primer for the synthesis of Melittin (48mer)

<400> SEQUENCE: 17
ggtatcggtg cggttctgaa agttctgacc accggtctgc cggcgctg                   48

<210> SEQ ID NO 18
<211> LENGTH: 58
<212> TYPE: DNA
<213> ORGANISM: Artificial Sequence
<220> FEATURE:
<223> OTHER INFORMATION: primer for the synthesis of Melittin (58mer)

<400> SEQUENCE: 18
cgaattctca ctgctgacgt ttacgtttga tccaagagat cagcgccggc agaccggt        58

<210> SEQ ID NO 19
<211> LENGTH: 45
<212> TYPE: DNA
<213> ORGANISM: Artificial Sequence
<220> FEATURE:
<223> OTHER INFORMATION: primer for the synthesis of PGQ (45mer)

<400> SEQUENCE: 19
ggtgttctgt ctaacgttat cggttacctg aaaaaactgg gtacc                      45
```

```
<210> SEQ ID NO 20
<211> LENGTH: 55
<212> TYPE: DNA
<213> ORGANISM: Artificial Sequence
<220> FEATURE:
<223> OTHER INFORMATION: primer for the synthesis of PGQ (55mer)

<400> SEQUENCE: 20
cgaattctca ctgtttcaga accgcgttca gcgcaccggt acccagtttt ttcag        55

<210> SEQ ID NO 21
<211> LENGTH: 59
<212> TYPE: DNA
<213> ORGANISM: Artificial Sequence
<220> FEATURE:
<223> OTHER INFORMATION: primer for the synthesis of Tachyplasin (59mer)

<400> SEQUENCE: 21
catgaaatgg tgcttccgtg tttgctaccg tggtatctgc taccgtcgtt gccgttgag    59

<210> SEQ ID NO 22
<211> LENGTH: 59
<212> TYPE: DNA
<213> ORGANISM: Artificial Sequence
<220> FEATURE:
<223> OTHER INFORMATION: primer for the synthesis of Tachyplasin (59mer)

<400> SEQUENCE: 22
aattctcaac ggcaacgacg gtagcagata ccccggtagc aaacacggaa gcaccattt    59

<210> SEQ ID NO 23
<211> LENGTH: 48
<212> TYPE: DNA
<213> ORGANISM: Artificial Sequence
<220> FEATURE:
<223> OTHER INFORMATION: primer for the synthesis of XPF (48mer)

<400> SEQUENCE: 23
ggttgggcgt ctaaaatcgg tcagaccctg ggtaaaatcg cgaaagtt                48

<210> SEQ ID NO 24
<211> LENGTH: 58
<212> TYPE: DNA
<213> ORGANISM: Artificial Sequence
<220> FEATURE:
<223> OTHER INFORMATION: primer for the synthesis of XPF (58mer)

<400> SEQUENCE: 24
cgaattctca tttcggctgg atcagttctt tcagaccaac tttcgcgatt ttacccag     58

<210> SEQ ID NO 25
<211> LENGTH: 30
<212> TYPE: DNA
<213> ORGANISM: Artificial Sequence
<220> FEATURE:
<223> OTHER INFORMATION: primer for the synthesis of F (30mer)

<400> SEQUENCE: 25
ggatccatat gtgcggtatt gtcggtatcg                                    30

<210> SEQ ID NO 26
<211> LENGTH: 25
<212> TYPE: DNA
<213> ORGANISM: Artificial Sequence
<220> FEATURE:
<223> OTHER INFORMATION: primer for the synthesis of F (25mer)
```

<400> SEQUENCE: 26
catatggcga gcttcaaata catcg                                    25

<210> SEQ ID NO 27
<211> LENGTH: 30
<212> TYPE: DNA
<213> ORGANISM: Artificial Sequence
<220> FEATURE:
<223> OTHER INFORMATION: primer for the synthesis of F' (30mer)

<400> SEQUENCE: 27
ggatccatat gtgcggtatt gtcggtatcg                               30

<210> SEQ ID NO 28
<211> LENGTH: 31
<212> TYPE: DNA
<213> ORGANISM: Artificial Sequence
<220> FEATURE:
<223> OTHER INFORMATION: primer for the synthesis of F' (31mer)

<400> SEQUENCE: 28
ggatccaata ttagcttcaa atacatcgct c                             31

<210> SEQ ID NO 29
<211> LENGTH: 30
<212> TYPE: DNA
<213> ORGANISM: Artificial Sequence
<220> FEATURE:
<223> OTHER INFORMATION: primer for the synthesis of F3 (30mer)

<400> SEQUENCE: 29
ggatccatat gtgcggtatt gtcggtatcg                               30

<210> SEQ ID NO 30
<211> LENGTH: 37
<212> TYPE: DNA
<213> ORGANISM: Artificial Sequence
<220> FEATURE:
<223> OTHER INFORMATION: primer for the synthesis of F3(HA) (37mer)

<400> SEQUENCE: 30
ggatccaata ttcgcatgcg cagcttcaaa tacatcg                       37

<210> SEQ ID NO 31
<211> LENGTH: 30
<212> TYPE: DNA
<213> ORGANISM: Artificial Sequence
<220> FEATURE:
<223> OTHER INFORMATION: primer for the synthesis of F3(CB) (30mer)

<400> SEQUENCE: 31
cgggatccac atgtggcgag cttcaaatac                               30

<210> SEQ ID NO 32
<211> LENGTH: 30
<212> TYPE: DNA
<213> ORGANISM: Artificial Sequence
<220> FEATURE:
<223> OTHER INFORMATION: primer for the synthesis of F4 (30mer)

<400> SEQUENCE: 32
ggatccatat gtgcggtatt gtcggtatcg                               30

<210> SEQ ID NO 33

<210> SEQ ID NO 33
<211> LENGTH: 24
<212> TYPE: DNA
<213> ORGANISM: Artificial Sequence
<220> FEATURE:
<223> OTHER INFORMATION: primer for the synthesis of F4(CB) (24mer)

<400> SEQUENCE: 33
gcggatccac atgtcggctt ccag                                    24

<210> SEQ ID NO 34
<211> LENGTH: 25
<212> TYPE: DNA
<213> ORGANISM: Artificial Sequence
<220> FEATURE:
<223> OTHER INFORMATION: primer for the synthesis of F3(HA) (25mer)

<400> SEQUENCE: 34
aatattgtcg gcttccagcg ggtag                                   25

<210> SEQ ID NO 35
<211> LENGTH: 23
<212> TYPE: DNA
<213> ORGANISM: Artificial Sequence
<220> FEATURE:
<223> OTHER INFORMATION: primer for the synthesis of BF (23mer)

<400> SEQUENCE: 35
catatgcttg ctgaaatcaa agg                                     23

<210> SEQ ID NO 36
<211> LENGTH: 30
<212> TYPE: DNA
<213> ORGANISM: Artificial Sequence
<220> FEATURE:
<223> OTHER INFORMATION: primer for the synthesis of BF (30mer)

<400> SEQUENCE: 36
aatattgcca gcaccctcct gtcctcggtg                              30

<210> SEQ ID NO 37
<211> LENGTH: 18
<212> TYPE: DNA
<213> ORGANISM: Artificial Sequence
<220> FEATURE:
<223> OTHER INFORMATION: primer for purF G49A mutant (18mer)

<400> SEQUENCE: 37
ttcgcttgcg cgaccact                                           18

<210> SEQ ID NO 38
<211> LENGTH: 26
<212> TYPE: DNA
<213> ORGANISM: Artificial Sequence
<220> FEATURE:
<223> OTHER INFORMATION: primer for purF N102L mutant (26mer)

<400> SEQUENCE: 38
tgcgaacggg tggagccgtt agactg                                  26

<210> SEQ ID NO 39
<211> LENGTH: 34
<212> TYPE: DNA
<213> ORGANISM: Artificial Sequence
<220> FEATURE:
<223> OTHER INFORMATION: Primers for the synthesis of kanR gene (34mer)

<400> SEQUENCE: 39

<210> SEQ ID NO 40
<211> LENGTH: 40
<212> TYPE: DNA
<213> ORGANISM: Artificial Sequence
<220> FEATURE:
<223> OTHER INFORMATION: primer for the synthesis of kanR gene (40mer)

<400> SEQUENCE: 40
cggatatcaa gcttggaaat gttgaatact catactcttc                                40

<210> SEQ ID NO 41
<211> LENGTH: 64
<212> TYPE: DNA
<213> ORGANISM: Artificial Sequence
<220> FEATURE:
<223> OTHER INFORMATION: APIDAECIN I gene

<400> SEQUENCE: 41
ggtaacaacc gtccggttta catcccgcag ccgcgtccgc cgcacccgcg tatctgagaa          60
ttcg                                                                       64

<210> SEQ ID NO 42
<211> LENGTH: 18
<212> TYPE: PRT
<213> ORGANISM: Artificial Sequence
<220> FEATURE:
<223> OTHER INFORMATION: APIDAECIN I peptide

<400> SEQUENCE: 42

Gly Asn Asn Arg Pro Val Tyr Ile Pro Gln Pro Arg Pro Pro His Pro
 1               5                  10                  15

Arg Ile

<210> SEQ ID NO 43
<211> LENGTH: 82
<212> TYPE: DNA
<213> ORGANISM: Artificial Sequence
<220> FEATURE:
<223> OTHER INFORMATION: BOMBININ gene

<400> SEQUENCE: 43
ggtatcggtg cgctgtctgc gaaaggtgcg ctgaaaggtc tggcgaaagg tctggcggaa          60
cacttcgcga actgagaatt cg                                                   82

<210> SEQ ID NO 44
<211> LENGTH: 24
<212> TYPE: PRT
<213> ORGANISM: Artificial Sequence
<220> FEATURE:
<223> OTHER INFORMATION: BOMBININE peptide

<400> SEQUENCE: 44

Gly Ile Gly Ala Leu Ser Ala Lys Gly Ala Leu Lys Gly Leu Ala Lys
 1               5                  10                  15

Gly Leu Ala Glu His Phe Ala Asn
            20

<210> SEQ ID NO 45
<211> LENGTH: 100
<212> TYPE: DNA
<213> ORGANISM: Artificial Sequence

```
<220> FEATURE:
<223> OTHER INFORMATION: CPFI gene

<400> SEQUENCE: 45
ggtttcgcgt ctttcctggg taaagcgctg aaagcgctga aagcggcgct gaaaatcggt    60
gcgaacgcgc tgggtggtgc gccgcagcag tgagaattcg                          100

<210> SEQ ID NO 46
<211> LENGTH: 30
<212> TYPE: PRT
<213> ORGANISM: Artificial Sequence
<220> FEATURE:
<223> OTHER INFORMATION: CPFI peptide

<400> SEQUENCE: 46

Gly Phe Ala Ser Phe Leu Gly Lys Ala Leu Lys Ala Leu Lys Ala Ala
 1               5                  10                  15

Leu Lys Ile Gly Ala Asn Ala Leu Gly Gly Ala Pro Gln Gln
             20                  25                  30

<210> SEQ ID NO 47
<211> LENGTH: 67
<212> TYPE: DNA
<213> ORGANISM: Artificial Sequence
<220> FEATURE:
<223> OTHER INFORMATION: DROSOCIN gene

<400> SEQUENCE: 47
ggtaaaccgc gtccgtactc tccgcgtccg acctctcacc cgcgtccgat cgcggtttga    60
gaattcg                                                              67

<210> SEQ ID NO 48
<211> LENGTH: 19
<212> TYPE: PRT
<213> ORGANISM: Artificial Sequence
<220> FEATURE:
<223> OTHER INFORMATION: DROSOCIN peptide

<400> SEQUENCE: 48

Gly Lys Pro Arg Pro Tyr Ser Pro Arg Pro Thr Ser His Pro Arg Pro
 1               5                  10                  15

Ile Ala Val

<210> SEQ ID NO 49
<211> LENGTH: 110
<212> TYPE: DNA
<213> ORGANISM: Artificial Sequence
<220> FEATURE:
<223> OTHER INFORMATION: HNP-I gene

<400> SEQUENCE: 49
gcatgccatg gcgtgctact gccgtatccc ggcgtgcatc gcgggtgagc gtcgttacgg    60
tacctgcatc taccagggtc gtctgtgggc gttctgctgc tgagaattcg               110

<210> SEQ ID NO 50
<211> LENGTH: 30
<212> TYPE: PRT
<213> ORGANISM: Artificial Sequence
<220> FEATURE:
<223> OTHER INFORMATION: HNP-I peptide

<400> SEQUENCE: 50

Ala Cys Tyr Cys Arg Ile Pro Ala Cys Ile Ala Gly Glu Arg Arg Tyr
```

```
            1               5              10              15
Gly Thr Cys Ile Tyr Gln Gly Arg Leu Trp Ala Phe Cys Cys
                20              25              30
```

<210> SEQ ID NO 51
<211> LENGTH: 53
<212> TYPE: DNA
<213> ORGANISM: Artificial Sequence
<220> FEATURE:
<223> OTHER INFORMATION: INDOLICIDIN gene

<400> SEQUENCE: 51

```
catgatcctg ccgtggaaat ggccgtggtg gccgtggcgt cgttgagaat tcg        53
```

<210> SEQ ID NO 52
<211> LENGTH: 13
<212> TYPE: PRT
<213> ORGANISM: Artificial Sequence
<220> FEATURE:
<223> OTHER INFORMATION: INDOLICIDIN peptide

<400> SEQUENCE: 52

```
Ile Leu Pro Trp Lys Trp Pro Trp Trp Pro Trp Arg Arg
 1               5              10
```

<210> SEQ ID NO 53
<211> LENGTH: 88
<212> TYPE: DNA
<213> ORGANISM: Artificial Sequence
<220> FEATURE:
<223> OTHER INFORMATION: MELITTIN gene

<400> SEQUENCE: 53

```
ggtatcggtg cggttctgaa agttctgacc accggtctgc cggcgctgat ctcttggatc    60
aaacgtaaac gtcagcagtg agaattcg                                       88
```

<210> SEQ ID NO 54
<211> LENGTH: 26
<212> TYPE: PRT
<213> ORGANISM: Artificial Sequence
<220> FEATURE:
<223> OTHER INFORMATION: MELLITIN peptide

<400> SEQUENCE: 54

```
Gly Ile Gly Ala Val Leu Lys Val Leu Thr Thr Gly Leu Pro Ala Leu
 1               5              10              15

Ile Ser Trp Ile Lys Arg Lys Arg Gln Gln
                20              25
```

<210> SEQ ID NO 55
<211> LENGTH: 103
<212> TYPE: DNA
<213> ORGANISM: Artificial Sequence
<220> FEATURE:
<223> OTHER INFORMATION: MSI-344(a) gene

<400> SEQUENCE: 55

```
tccggatcca tatgggtatc ggcaaattcc tgaaaaaggc taagaaattt ggtaaggcgt    60
tcgttaaaat cctgaaaaag taatgaagga gatatattaa tgc                     103
```

<210> SEQ ID NO 56
<211> LENGTH: 23
<212> TYPE: PRT
<213> ORGANISM: Artificial Sequence

```
<220> FEATURE:
<223> OTHER INFORMATION: MSI-344(a) peptide

<400> SEQUENCE: 56

Met Gly Ile Gly Lys Phe Leu Lys Lys Ala Lys Lys Phe Gly Lys Ala
 1               5                  10                  15

Phe Val Lys Ile Leu Lys Lys
            20

<210> SEQ ID NO 57
<211> LENGTH: 100
<212> TYPE: DNA
<213> ORGANISM: Artificial Sequence
<220> FEATURE:
<223> OTHER INFORMATION: MSI-344(b) gene

<400> SEQUENCE: 57
ggatcccggg atcggcaaat tcctgaaaaa ggctaagaaa tttggtaagg cgttcgttaa    60
aatcctgaaa aagtaatgaa ggagatatat taatggatcc                          100

<210> SEQ ID NO 58
<211> LENGTH: 22
<212> TYPE: PRT
<213> ORGANISM: Artificial Sequence
<220> FEATURE:
<223> OTHER INFORMATION: MSI-344(b) peptide

<400> SEQUENCE: 58

Gly Ile Gly Lys Phe Leu Lys Lys Ala Lys Lys Phe Gly Lys Ala Phe
 1               5                  10                  15

Val Lys Ile Leu Lys Lys
            20

<210> SEQ ID NO 59
<211> LENGTH: 88
<212> TYPE: DNA
<213> ORGANISM: Artificial Sequence
<220> FEATURE:
<223> OTHER INFORMATION: PGQ gene

<400> SEQUENCE: 59
ggtgttctgt ctaacgttat cggtatcggt tacctgaaaa aactgggtac cggtgcgctg    60
aacgcggttc tgaaacagtg agaattcg                                       88

<210> SEQ ID NO 60
<211> LENGTH: 26
<212> TYPE: PRT
<213> ORGANISM: Artificial Sequence
<220> FEATURE:
<223> OTHER INFORMATION: PGQ peptide

<400> SEQUENCE: 60

Gly Val Leu Ser Asn Val Ile Gly Ile Gly Tyr Leu Lys Lys Leu Gly
 1               5                  10                  15

Thr Gly Ala Leu Asn Ala Val Leu Lys Gln
            20                  25

<210> SEQ ID NO 61
<211> LENGTH: 65
<212> TYPE: DNA
<213> ORGANISM: Artificial Sequence
<220> FEATURE:
<223> OTHER INFORMATION: TACHYPLASIN I gene
```

<210> SEQ ID NO 62
<211> LENGTH: 17
<212> TYPE: PRT
<213> ORGANISM: Artificial Sequence
<220> FEATURE:
<223> OTHER INFORMATION: TACHYPLASIN I peptide

<400> SEQUENCE: 62

```
Lys Trp Cys Phe Arg Val Cys Tyr Arg Gly Ile Cys Tyr Arg Cys
 1               5                  10                  15
Arg
```

<210> SEQ ID NO 63
<211> LENGTH: 85
<212> TYPE: DNA
<213> ORGANISM: Artificial Sequence
<220> FEATURE:
<223> OTHER INFORMATION: XPF gene

<400> SEQUENCE: 63

```
ggttgggcgt ctaaaatcgg tcagaccctg gtaaaatcg cgaaagttgg tctgaaagaa      60
ctgatccagc cgaaatgaga attcg                                            85
```

<210> SEQ ID NO 64
<211> LENGTH: 25
<212> TYPE: PRT
<213> ORGANISM: Artificial Sequence
<220> FEATURE:
<223> OTHER INFORMATION: XPF peptide

<400> SEQUENCE: 64

```
Gly Trp Ala Ser Lys Ile Gly Gln Thr Leu Gly Lys Ile Ala Lys Val
 1               5                  10                  15

Gly Leu Lys Glu Leu Ile Gln Pro Lys
            20                  25
```

<210> SEQ ID NO 65
<211> LENGTH: 129
<212> TYPE: DNA
<213> ORGANISM: Artificial Sequence
<220> FEATURE:
<223> OTHER INFORMATION: BUFORIN I gene

<400> SEQUENCE: 65

```
ggcgcgggac gcggcaaaca aggaggcaaa gtgcgggcta aggccaagac ccgctcatcc      60
cgggcagggc tccagttccc ggtcggccgt gtgcacaggc tcctccgcaa gggcaactac     120
taaggatcc                                                             129
```

<210> SEQ ID NO 66
<211> LENGTH: 40
<212> TYPE: PRT
<213> ORGANISM: Artificial Sequence
<220> FEATURE:
<223> OTHER INFORMATION: BUFORIN I peptide

<400> SEQUENCE: 66

```
Gly Ala Gly Arg Gly Lys Gln Gly Gly Lys Val Arg Ala Lys Ala Lys
 1               5                  10                  15
```

Thr Arg Ser Ser Arg Ala Gly Leu Gln Phe Pro Val Gly Arg Val His
            20                  25                  30

Arg Leu Leu Arg Lys Gly Asn Tyr
            35                  40

<210> SEQ ID NO 67
<211> LENGTH: 93
<212> TYPE: DNA
<213> ORGANISM: Artificial Sequence
<220> FEATURE:
<223> OTHER INFORMATION: BUFORIN II gene

<400> SEQUENCE: 67
gggacccgtt cctcccgtgc tggtctgcag ttcccggttg gtcgtgttca ccgtctgctg        60
cgtaaataat gaaggagata tattaatgga tcc                                    93

<210> SEQ ID NO 68
<211> LENGTH: 22
<212> TYPE: PRT
<213> ORGANISM: Artificial Sequence
<220> FEATURE:
<223> OTHER INFORMATION: BUFORIN II peptide

<400> SEQUENCE: 68

Gly Thr Arg Ser Ser Arg Ala Gly Leu Gln Phe Pro Val Gly Arg Val
 1               5                  10                  15

His Arg Leu Leu Arg Lys
            20

<210> SEQ ID NO 69
<211> LENGTH: 81
<212> TYPE: DNA
<213> ORGANISM: Artificial Sequence
<220> FEATURE:
<223> OTHER INFORMATION: BUFORIN IIa gene

<400> SEQUENCE: 69
gggcgtgctg gtctgcagtt cccggttggt cgtgttcacc gtctgctgcg taaataatga        60
aggagatata ttaatggatc c                                                 81

<210> SEQ ID NO 70
<211> LENGTH: 18
<212> TYPE: PRT
<213> ORGANISM: Artificial Sequence
<220> FEATURE:
<223> OTHER INFORMATION: BUFORIN IIa peptide

<400> SEQUENCE: 70

Gly Arg Ala Gly Leu Gln Phe Pro Val Gly Arg Val His Arg Leu Leu
 1               5                  10                  15

Arg Lys

<210> SEQ ID NO 71
<211> LENGTH: 93
<212> TYPE: DNA
<213> ORGANISM: Artificial Sequence
<220> FEATURE:
<223> OTHER INFORMATION: BUFORIN IIb gene

<400> SEQUENCE: 71
gggcgtgctg gtctgcagtt cccggttggt cgcctgctgc gccgtctgct gcgtcgcctg        60
ctgcgctaat gaaggagata tattaatgga tcc                                    93

<210> SEQ ID NO 72
<211> LENGTH: 22
<212> TYPE: PRT
<213> ORGANISM: Artificial Sequence
<220> FEATURE:
<223> OTHER INFORMATION: BUFORIN IIb peptide

<400> SEQUENCE: 72

Gly Arg Ala Gly Leu Gln Phe Pro Val Gly Arg Leu Leu Arg Arg Leu
1               5                   10                  15

Leu Arg Arg Leu Leu Arg
            20

<210> SEQ ID NO 73
<211> LENGTH: 186
<212> TYPE: DNA
<213> ORGANISM: Artificial Sequence
<220> FEATURE:
<223> OTHER INFORMATION: F gene

<400> SEQUENCE: 73
catatgtgcg gtattgtcgg tatcgccggt gttatgccgg ttaaccagtc gatttatgat    60
gccttaacgg tgcttcagca tcgcggtcag gatgccgccg gcatcatcac catagatgcc   120
aataactgct tccgtttgcg taaagcgaac gggctggtga gcgatgtatt tgaagctcgc   180
catatg                                                              186

<210> SEQ ID NO 74
<211> LENGTH: 61
<212> TYPE: PRT
<213> ORGANISM: Artificial Sequence
<220> FEATURE:
<223> OTHER INFORMATION: F peptide

<400> SEQUENCE: 74

Met Cys Gly Ile Val Gly Ile Ala Gly Val Met Pro Val Asn Gln Ser
1               5                   10                  15

Ile Tyr Asp Ala Leu Thr Val Leu Gln His Arg Gly Gln Asp Ala Ala
            20                  25                  30

Gly Ile Ile Thr Ile Asp Ala Asn Asn Cys Phe Arg Leu Arg Lys Ala
        35                  40                  45

Asn Gly Leu Val Ser Asp Val Phe Glu Ala Arg His Met
    50                  55                  60

<210> SEQ ID NO 75
<211> LENGTH: 183
<212> TYPE: DNA
<213> ORGANISM: Artificial Sequence
<220> FEATURE:
<223> OTHER INFORMATION: F' gene

<400> SEQUENCE: 75
catatgtgcg gtattgtcgg tatcgccggt gttatgccgg ttaaccagtc gatttatgat    60
gccttaacgg tgcttcagca tcgcggtcag gatgccgccg gcatcatcac catagatgcc   120
aataactgct tccgtttgcg taaagcgaac gcgctggtga gcgatgtatt tgaagctaat   180
att                                                                 183

<210> SEQ ID NO 76
<211> LENGTH: 59
<212> TYPE: PRT

<213> ORGANISM: Artificial Sequence
<220> FEATURE:
<223> OTHER INFORMATION: F' peptide

<400> SEQUENCE: 76

Met Cys Gly Ile Val Gly Ile Ala Gly Val Met Pro Val Asn Gln Ser
 1               5                  10                  15

Ile Tyr Asp Ala Leu Thr Val Leu Gln His Arg Gly Gln Asp Ala Ala
            20                  25                  30

Gly Ile Ile Thr Ile Asp Ala Asn Asn Cys Phe Arg Leu Arg Lys Ala
        35                  40                  45

Asn Ala Leu Val Ser Asp Val Phe Glu Ala Asn
    50                  55

<210> SEQ ID NO 77
<211> LENGTH: 192
<212> TYPE: DNA
<213> ORGANISM: Artificial Sequence
<220> FEATURE:
<223> OTHER INFORMATION: F3(HA) gene

<400> SEQUENCE: 77
catatgtgcg gtattgtcgg tatcgccggt gttatgccgg ttaaccagtc gatttatgat      60
gccttaacgg tgcttcagca tcgcggtcag gatgccgccg gcatcatcac catagatgcc     120
aataactgct tccgtttgcg taaagcgaac gcgctggtga gcgatgtatt tgaagctgcg     180
catgcgaata tt                                                        192

<210> SEQ ID NO 78
<211> LENGTH: 62
<212> TYPE: PRT
<213> ORGANISM: Artificial Sequence
<220> FEATURE:
<223> OTHER INFORMATION: F3(HA) peptide

<400> SEQUENCE: 78

Met Cys Gly Ile Val Gly Ile Ala Gly Val Met Pro Val Asn Gln Ser
 1               5                  10                  15

Ile Tyr Asp Ala Leu Thr Val Leu Gln His Arg Gly Gln Asp Ala Ala
            20                  25                  30

Gly Ile Ile Thr Ile Asp Ala Asn Asn Cys Phe Arg Leu Arg Lys Ala
        35                  40                  45

Asn Ala Leu Val Ser Asp Val Phe Glu Ala Ala His Ala Asn
    50                  55                  60

<210> SEQ ID NO 79
<211> LENGTH: 145
<212> TYPE: DNA
<213> ORGANISM: Artificial Sequence
<220> FEATURE:
<223> OTHER INFORMATION: F3(CB) gene

<400> SEQUENCE: 79
catatgtgcg gtattgtcgg tatcgccggt gttatgccgg ttaaccagtc gatttatgat      60
gccttaacgg tgcttcagca tcgcggtcag gatgccgccg gcgctggtga gcgatgtatt     120
tgaagctcgc cacatgtgga tcccg                                          145

<210> SEQ ID NO 80
<211> LENGTH: 61
<212> TYPE: PRT
<213> ORGANISM: Artificial Sequence

```
<220> FEATURE:
<223> OTHER INFORMATION: F3(CB) peptide

<400> SEQUENCE: 80

Met Cys Gly Ile Val Gly Ile Ala Gly Val Met Pro Val Asn Gln Ser
 1               5                  10                  15

Ile Tyr Asp Ala Leu Thr Val Leu Gln His Arg Gly Gln Asp Ala Ala
            20                  25                  30

Gly Ile Ile Thr Ile Asp Ala Asn Asn Cys Phe Arg Leu Arg Lys Ala
        35                  40                  45

Asn Ala Leu Val Ser Asp Val Phe Glu Ala Arg His Met
    50                  55                  60

<210> SEQ ID NO 81
<211> LENGTH: 462
<212> TYPE: DNA
<213> ORGANISM: Artificial Sequence
<220> FEATURE:
<223> OTHER INFORMATION: F4(HA) gene

<400> SEQUENCE: 81
catatgtgcg gtattgtcgg tatcgccggt gttatgccgg ttaaccagtc gatttatgat     60
gccttaacgg tgcttcagca tcgcggtcag gatgccgccg gcatcatcac catagatgcc    120
ataactgct tccgtttgcg taaagcgaac gggctggtga gcgatgtatt tgaagctcgc    180
catatgcagc gtttgcaggg caatatgggc attggtcatg tgcgttaccc cacggctggc    240
agctccagcg cctctgaagc gcagccgttt tacgttaact ccccgtatgg cattacgctt    300
gcccacatcg gcaatctgac caacgctcac gagttgcgta aaaaactgtt tgaagaaaaa    360
cgccgccaca tcaacaccac ttccgactcg gaaattctgc ttaatatctt cgccagcgag    420
ctggacaact ccgccacta cccgctggaa gccgacaata tt                       462

<210> SEQ ID NO 82
<211> LENGTH: 152
<212> TYPE: PRT
<213> ORGANISM: Artificial Sequence
<220> FEATURE:
<223> OTHER INFORMATION: F4(HA) peptide

<400> SEQUENCE: 82

Met Cys Gly Ile Val Gly Ile Ala Gly Val Met Pro Val Asn Gln Ser
 1               5                  10                  15

Ile Tyr Asp Ala Leu Thr Val Leu Gln His Arg Gly Gln Asp Ala Ala
            20                  25                  30

Gly Ile Ile Thr Ile Asp Ala Asn Asn Cys Phe Arg Leu Arg Lys Ala
        35                  40                  45

Asn Gly Leu Val Ser Asp Val Phe Glu Ala Arg His Met Gln Arg Leu
    50                  55                  60

Gln Gly Asn Met Gly Ile Gly His Val Arg Tyr Pro Thr Ala Gly Ser
65                  70                  75                  80

Ser Ser Ala Ser Glu Ala Gln Pro Phe Tyr Val Asn Ser Pro Tyr Gly
                85                  90                  95

Ile Thr Leu Ala His Ile Gly Asn Leu Thr Asn Ala His Glu Leu Arg
            100                 105                 110

Lys Lys Leu Phe Glu Glu Lys Arg Arg His Ile Asn Thr Thr Ser Asp
        115                 120                 125

Ser Glu Ile Leu Leu Asn Ile Phe Ala Ser Glu Leu Asp Asn Phe Arg
    130                 135                 140
```

<210> SEQ ID NO 83
<211> LENGTH: 462
<212> TYPE: DNA
<213> ORGANISM: Artificial Sequence
<220> FEATURE:
<223> OTHER INFORMATION: F4a(HA) gene

<400> SEQUENCE: 83

```
catatgtgcg gtattgtcgg tatcgccggt gttatgccgg ttaaccagtc gatttatgat    60
gccttaacgg tgcttcagca tcgcggtcag gatgccgccg gcatcatcac catagatgcc   120
aataactgct tccgtttgcg taaagcgaac gcgctggtga gcgatgtatt tgaagctcgc   180
catatgcagc gtttgcaggg caatatgggc attggtcatg tgcgttaccc cacggctggc   240
agctccagcg cctctgaagc gcagccgttt tacgttaact ccccgtatgg cattacgctt   300
gcccacatcg gcaatctgac caacgctcac gagttgcgta aaaaactgtt tgaagaaaaa   360
cgccgccaca tcaacaccac ttccgactcg gaaattctgc ttaatatctt cgccagcgag   420
ctggacaact tccgccacta cccgctggaa gccgacaata tt                      462
```

<210> SEQ ID NO 84
<211> LENGTH: 152
<212> TYPE: PRT
<213> ORGANISM: Artificial Sequence
<220> FEATURE:
<223> OTHER INFORMATION: F4a(HA) peptide

<400> SEQUENCE: 84

Met Cys Gly Ile Val Gly Ile Ala Gly Val Met Pro Val Asn Gln Ser
  1               5                  10                  15
Ile Tyr Asp Ala Leu Thr Val Leu Gln His Arg Gly Gln Asp Ala Ala
             20                  25                  30
Gly Ile Ile Thr Ile Asp Ala Asn Asn Cys Phe Arg Leu Arg Lys Ala
         35                  40                  45
Asn Ala Leu Val Ser Asp Val Phe Glu Ala Arg His Met Gln Arg Leu
     50                  55                  60
Gln Gly Asn Met Gly Ile Gly His Val Arg Tyr Pro Thr Ala Gly Ser
 65                  70                  75                  80
Ser Ser Ala Ser Glu Ala Gln Pro Phe Tyr Val Asn Ser Pro Tyr Gly
                 85                  90                  95
Ile Thr Leu Ala His Ile Gly Asn Leu Thr Asn Ala His Glu Leu Arg
            100                 105                 110
Lys Lys Leu Phe Glu Glu Lys Arg Arg His Ile Asn Thr Thr Ser Asp
        115                 120                 125
Ser Glu Ile Leu Leu Asn Ile Phe Ala Ser Glu Leu Asp Asn Phe Arg
    130                 135                 140
His Tyr Pro Leu Glu Ala Asp Asn
145                 150

<210> SEQ ID NO 85
<211> LENGTH: 462
<212> TYPE: DNA
<213> ORGANISM: Artificial Sequence
<220> FEATURE:
<223> OTHER INFORMATION: F4a(CB) gene

<400> SEQUENCE: 85

```
catatgtgcg gtattgtcgg tatcgccggt gttatgccgg ttaaccagtc gatttatgat      60
gccttaacgg tgcttcagca tcgcggtcag gatgccgccg gcatcatcac catagatgcc    120
aataactgct tccgtttgcg taaagcgaac gggctggtga gcgatgtatt tgaagctcgc    180
catatgcagc gtttgcaggg caatatgggc attggtcatg tgcgttaccc cacggctggc    240
agctccagcg cctctgaagc gcagccgttt tacgttaact ccccgtatgg cattacgctt    300
gcccacatcg gcaatctgac caacgctcac gagttgcgta aaaaactgtt tgaagaaaaa    360
cgccgccaca tcaacaccac ttccgactcg gaaattctgc ttaatatctt cgccagcgag    420
ctggacaact tccgccacta cccgctggaa gccgacatgt gg                       462
```

<210> SEQ ID NO 86
<211> LENGTH: 152
<212> TYPE: PRT
<213> ORGANISM: Artificial Sequence
<220> FEATURE:
<223> OTHER INFORMATION: F5 gene

<400> SEQUENCE: 86

```
Met Cys Gly Ile Val Gly Ile Ala Gly Val Met Pro Val Asn Gln Ser
  1               5                  10                  15

Ile Tyr Asp Ala Leu Thr Val Leu Gln His Arg Gly Gln Asp Ala Ala
             20                  25                  30

Gly Ile Ile Thr Ile Asp Ala Asn Asn Cys Phe Arg Leu Arg Lys Ala
         35                  40                  45

Asn Ala Leu Val Ser Asp Val Phe Glu Ala Arg His Met Gln Arg Leu
     50                  55                  60

Gln Gly Asn Met Gly Ile Gly His Val Arg Tyr Pro Thr Ala Gly Ser
 65                  70                  75                  80

Ser Ser Ala Ser Glu Ala Gln Pro Phe Tyr Val Asn Ser Pro Tyr Gly
                 85                  90                  95

Ile Thr Leu Ala His Ile Gly Asn Leu Thr Asn Ala His Glu Leu Arg
            100                 105                 110

Lys Lys Leu Phe Glu Glu Lys Arg Arg His Ile Asn Thr Thr Ser Asp
        115                 120                 125

Ser Glu Ile Leu Leu Asn Ile Phe Ala Ser Glu Leu Asp Asn Phe Arg
    130                 135                 140

His Tyr Pro Leu Glu Ala Asp Met
145                 150
```

<210> SEQ ID NO 87
<211> LENGTH: 282
<212> TYPE: DNA
<213> ORGANISM: Artificial Sequence
<220> FEATURE:
<223> OTHER INFORMATION: F5 gene

<400> SEQUENCE: 87

```
catatgcagc gtttgcaggg caatatgggc attggtcatg tgcgttaccc cacggctggc      60
agctccagcg cctctgaagc gcagccgttt tacgttaact ccccgtatgg cattacgctt    120
gcccacatcg gcaatctgac caacgctcac gagttgcgta aaaaactgtt tgaagaaaaa    180
cgccgccaca tcaacaccac ttccgactcg gaaattctgc ttaatatctt cgccagcgag    240
ctggacaact tccgccacta cccgctggaa gccgacaata tt                       282
```

<210> SEQ ID NO 88

```
<211> LENGTH: 92
<212> TYPE: PRT
<213> ORGANISM: Artificial Sequence
<220> FEATURE:
<223> OTHER INFORMATION: F5 peptide

<400> SEQUENCE: 88

Met Gln Arg Leu Gln Gly Asn Met Gly Ile Gly His Val Arg Tyr Pro
 1               5                  10                  15

Thr Ala Gly Ser Ser Ala Ser Glu Ala Gln Pro Phe Tyr Val Asn
             20                  25                  30

Ser Pro Tyr Gly Ile Thr Leu Ala His Ile Gly Asn Leu Thr Asn Ala
         35                  40                  45

His Glu Leu Arg Lys Lys Leu Phe Glu Lys Arg Arg His Ile Asn
 50                  55                  60

Thr Thr Ser Asp Ser Glu Ile Leu Leu Asn Ile Phe Ala Ser Glu Leu
 65                  70                  75                  80

Asp Asn Phe Arg His Tyr Pro Leu Glu Ala Asp Asn
                 85                  90

<210> SEQ ID NO 89
<211> LENGTH: 138
<212> TYPE: DNA
<213> ORGANISM: Artificial Sequence
<220> FEATURE:
<223> OTHER INFORMATION: BF gene

<400> SEQUENCE: 89
catatgcttg ctgaaatcaa aggcttaaat gaagaatgcg gcgttttttgg gatttgggga      60 catgaagaag ccccgcaaat cacgtattac ggtctccaca gccttcagca ccgaggacag     120
gagggtgctg gcaatatt                                                    138

<210> SEQ ID NO 90
<211> LENGTH: 44
<212> TYPE: PRT
<213> ORGANISM: Artificial Sequence
<220> FEATURE:
<223> OTHER INFORMATION: BF peptide

<400> SEQUENCE: 90

Met Leu Ala Glu Ile Lys Gly Leu Asn Glu Glu Cys Gly Val Phe Gly
 1               5                  10                  15

Ile Trp Gly His Glu Glu Ala Pro Gln Ile Thr Tyr Tyr Gly Leu His
             20                  25                  30

Ser Leu Gln His Arg Gly Gln Glu Gly Ala Gly Asn
         35                  40

<210> SEQ ID NO 91
<211> LENGTH: 15
<212> TYPE: DNA
<213> ORGANISM: Artificial Sequence
<220> FEATURE:
<223> OTHER INFORMATION: RBS binding site (15mer)

<400> SEQUENCE: 91
taatgaagga gatat                                                        15

<210> SEQ ID NO 92
<211> LENGTH: 24
<212> TYPE: DNA
<213> ORGANISM: Artificial Sequence
<220> FEATURE:
```

-continued

```
<223> OTHER INFORMATION: AseI and RBS binding sites

<400> SEQUENCE: 92
aagtaatgaa ggagatatat taat                                              24

<210> SEQ ID NO 93
<211> LENGTH: 24
<212> TYPE: DNA
<213> ORGANISM: Artificial Sequence
<220> FEATURE:
<223> OTHER INFORMATION: AseI and RBS binding sites

<400> SEQUENCE: 93
ttcattacat cctctatata atta                                              24
```

US 6,699,689 B1

MASS PRODUCTION METHOD OF ANTIMICROBIAL PEPTIDE AND DNA CONSTRUCT AND EXPRESSION SYSTEM THEREOF

TECHNICAL FIELD AND BACKGROUND ART

The present invention relates to the recombinant DNA technology. The present invention also relates to the mass-production of antimicrobial materials from microorganisms and a DNA construct and vector system. Biologically active peptide (antimicrobial peptide hereinafter) has little chance to develop resistance since the antimicrobial peptides show activity by a mechanism that is totally different from that of conventional antibiotics which have a serious problem of developing resistance. Therefore, the antimicrobial peptides have a high industrial applicability in the fields of pharmaceutics and the food industry.

The main obstacle in the industrial use of the antimicrobial peptide, however, is the difficulty in economical mass-production of the antimicrobial peptides. For instance, the production of the antimicrobial peptides by chemical synthesis is not economical. Also, there have been attempts to produce antimicrobial peptides by genetic engineering using microorganisms, in this case, however, the expression levels of the antimicrobial peptides are very low.

U.S. Pat. No. 5,206,154 provides a DNA construct which comprises a polypeptide gene which is capable of suppressing the bactericidal effect of cecropin, and a cecropin gene fused to the polypeptide gene. An example of such polypeptide disclosed in the patent is the araB gene.

U.S. Pat. No. 5,593,866 provides a method for a microbial production of a cationic antimicrobial peptide, wherein the cationic peptides is expressed as a fusion to an anionic peptide to avoid degradation by a bacterial protease.

DISCLOSURE OF THE INVENTION

The present invention provides a DNA construct to mass-produce a antimicrobial peptides. The present invention also provides a DNA construct that can produce and recover antimicrobial peptides effectively from microorganisms.

Also, the present invention provides gene multimers that can increase the efficiency of expression, separation and purification of desired peptides and the construction method of such construct.

Further, the present invention provides an expression vector to mass-produce antimicrobial peptides from microorganisms.

Further, the present invention provides a method to mass-produce antimicrobial peptides form microorganisms.

BRIEF DESCRIPTION OF THE DRAWINGS

FIGS. 1A, 1B, 1C, 1D, 1E and 1F, herein referred to collectively as FIG. 1, are a nucleotide sequence coding for an antimicrobial peptide of the present invention.

FIGS. 2A, 2B, 2C and 2D, herein referred to collectively as FIG. 2, are a nucleotide sequence coding for a fusion partner.

FIGS. 6A and 6B, herein referred to collectively as FIG. 6, are a scheme of the construction of the pGNX2 vector.

FIGS. 14a, 14b, 14c and 14d are SDS-PAGE electrophoretic analyses of the lysates of the transformants expressing various antimicrobial peptides by an induction with lactose.

DETAILED DESCRIPTION OF THE INVENTION

Figure 3A:
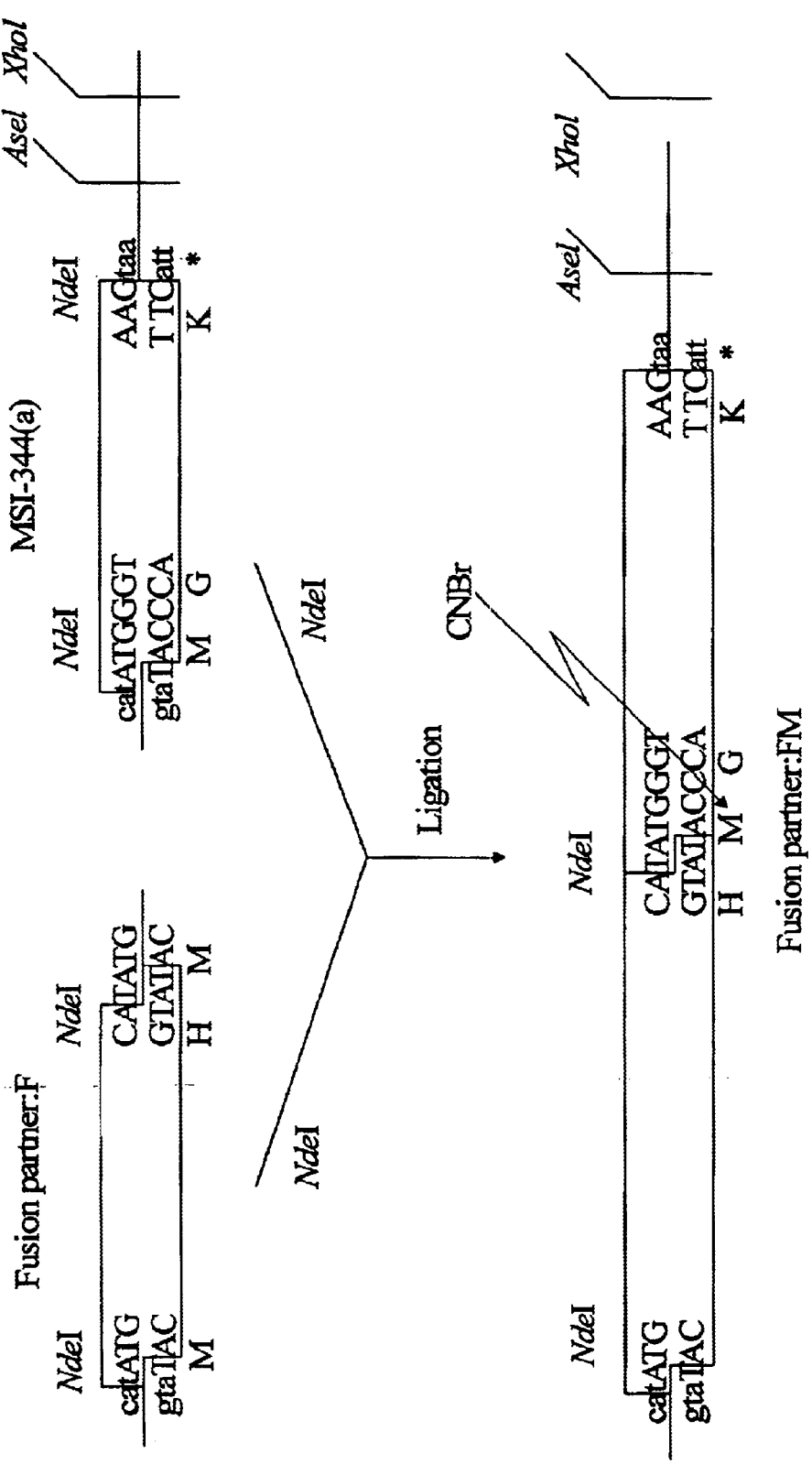
FIGS. 3A and 3B, herein referred to collectively as FIG. 3, are a scheme of a fusion method between the fusion partner and the MSI-344 gene by generating a sequence encoding producing CNBr cleavage site.

The present invention relates to a DNA construct for mass-producing antimicrobial peptides effectively in *E. coli* or other prokaryotes.

One of the essential conditions for mass production of the antimicrobial peptides from microorganisms is to efficiently neutralize the toxicity of the antimicrobial peptides against the microorganisms. To this end, the present invention provides a DNA construct in which a whole gene, partial or derivatives of the purF gene (glutamine pyrophosphoribosyl pyrophosphate amidotransferase; Genbank No.: X12423) (Tso et al., J. Biol. Chem., 257: 3525, 1982, Makaroff et al., J. Bio. Chem., 258: 10586, 1983) is fused as a fusion partner to the gene coding for antimicrobial peptides.

The derivatives of purF gene used as a fusion partner in the DNA construct according to the present invention allows mass-production of the antimicrobial peptides as a fused polypeptide with purF derivatives in *Escherichia coli* without killing the host cells. Therefore, it is possible to mass-produce the desired antimicrobial peptides from the host microorganisms using a strong expression system since they are not lethal to the host cell. In the case of using a fusion partner according to the present invention to express peptides, it is possible to cleave and separate the antimicrobial peptides from the fusion protein by using a protease or other chemicals. To achieve this, for instance it is possible to insert a DNA sequence between the fusion partner and antimicrobial peptide genes encoding the cleavage site for proteases such as Factor Xa or enterokinase or chemicals such as CNBr or hydroxylamine.

For instance, to provide a CNBr cleavage site, restriction enzyme site containing Met codon (ATG) with correct leading frame such as Afl III, Bsm I, BspH I, BspLU11 I, Nco I, Nde I, Nsi I, Ppu10 I, Sph I, Sty I, or their isoschizomers could be inserted into the 3' end of the fusion partner. It is possible to make in-frame fusion of the fusion partner and the gene coding for antimicrobial peptide by inserting the restriction enzyme site into the 5 end of the gene coding for antimicrobial peptide that produces a compatible end to the enzyme site of the fusion partner.

It is also possible to insert a DNA sequence coding for Asn-Gly between the fusion partner and antimicrobial peptide genes. For instance, two genes can be fused by the following method. After inserting a restriction enzyme or isoschizomer site containing an Asn codon with correct reading frame at the 3' end of the fusion partner, the fusion partner is cleaved by the enzyme. At the 5' end of the gene coding for antimicrobial peptide, a restriction enzyme site containing a Gly codon with correct reading frame that produces a compatible or blunt end with the corresponding site of the fusion partner is inserted and cleaved with the corresponding enzyme. The two cleaved DNA fragments may be connected to produce the fused gene. The genetic construct according to the present invention may be inserted into the host cell by cloning into any kind of expression vector, that is conventionally used in this field such as plasmid, virus or other vehicles that can be used to insert or incorporate the structural genes.

The present invention relates to a multimer that can increase the expression level by increasing the copy number of the gene of the required product and which can be separated and purified conveniently and the preparation method thereof.

The multimer according to the present invention is constructed by the following units.
1) A first restriction enzyme site that can generate an initiation codon Met, 2) a structural gene, 3) a ribosome binding site (RBS), and 4) a second restriction enzyme site generating a cohesive end which can be in-frame fused to the cohesive end generated by the first restriction enzyme and which can generate the initiation codon. Here, the stop codon and the RBS of the structural gene may overlap by ca. 2 bp or may be separated as far as 500 bp. The distance between the RBS and the second restriction enzyme site that can generate the initiation codon may be ca. 5 to 30 bp. The 3' and 5' ends of the multimer may be cleaved by the first or second restriction enzyme, respectively.

The multimer according to the present invention may be prepared by a variety of techniques known in the field of genetic engineering. One of the examples of such preparation method is given below.

After cleaving the units of a gene given above by the first and second restriction enzymes, the cleaved units is connected to produce a mixture containing multimers that include each unit with the same direction and multimers that have more than one unit with reverse direction. Since the multimers that contain more than one unit with reverse direction will have the first or second restriction enzyme site regenerated at the connection site, the multimer mixture may be cleaved simultaneously by the first and second restriction enzymes and separated by agarose gel electrophoresis, for instance, to separate the multimers those have units with the same direction only. The multimer according to the present invention is a transcriptionally fused multimer. This means that the repeated genes are transcribed into a single mRNA, but the gene expression product is not connected. In other words, the multimer is translated into many copies of a single product, In the case of the conventional translationally fused multimer, the desired product is present as a concatemer in a single polynucleotide, and an additional cleavage process is necessary to obtain the desired active product in case that the expression product is a fusion protein, it requires a greater amount of reagent to cleave only with lower efficiency when compared to the transcriptionally fused multimer. Compared to the translationally fused multimer, the expressed multimer of the present invention does not require additional cleavage processes or in the case it requires cleavage processes such as fused proteins, the amount of the reagent for the cleavage may be reduced since the number of peptide bonds to be cleaved per mole of the fused peptide is relatively smaller than the translationally fused multimer.

The multimer of the present invention may increase the gene expression in the host cell, have advantages in cleaving and purifying the desired product, and express in the host more efficiently when compared to the monomer. The multimer and the preparation method thereof are not limited in preparing peptides or fusion peptides. It can be widely applicable in expressing the unfused or fused gene coding for enzymes, hormones and antimicrobial polypeptides in microorganism.

Therefore, it is desirable to produce the DNA construct of the present invention in the form of transcriptionally fused multimer. In the case of preparing the DNA construct of the present invention in the form of transcriptionally fused multimer, it is advantageous to cleave and purify the products, and the multimer may be expressed in the host more efficiently than the monomer.

The present invention also relates to the expression vector that may induce the expression of foreign genes by lactose which is more economical than IPTG.

The expression vector according to the present invention is composed of high copy number replication origin, strong promoter and structural gene, and does not include lacI$^q$ gene.

The replication origin may be colE1 or p15A in the present invention. Examples of the strong promoters include tac, trc, trp, T7Φ10, $P_L$, other inducible or constitutive promoters in the microorganisms. Additionally, a selection marker gene that may be used to select the transformants of the vector may be included. These marker genes include antibiotic resistant genes against antibiotics such as ampicillin, kanamycin, tetracyline and chloramphenicol, or the genes that complement the auxotrophy of the host. Gene expression using the expression vector according to the present invention can be induced efficiently by adding lactose instead of IPTG preferably by adding IPTG and lactose simultaneously.

As an example, after transforming the plasmid containing the structural gene into the host cells, transformants are primary-cultured for 5 to 18 hours at 30–37° C. in a culture medium that include 50–300 µg/ml kanamycin. Afterwards, they are diluted to 1% (v/v) in a fresh media and cultured at 30–37° C. To induce the expression, 0.01 mM–10 mM IPTG is added when the $OD_{600}$ reaches 0.2–2 in case of IPTG induction, or 0.2–2% lactose is added when the $OD_{600}$ reaches 0.2–2, or at the time of inoculation in the case of lactose induction. IPTG and lactose can be used simultaneously with a significantly reduced amount of IPTG. Additionally, it is desirable to include a transcriptional terminator in the expression vector according to the present invention.

It is possible to obtain the expression product as an inclusion bodies using the expression vector of the present invention. This property is useful in producing a product lethal to the host.

A vector containing a structural gene of the present invention may be transformed into microorganisms by using conventional methods used in the fields of the present invention. For instance, the transformation may be achieved by CaCl₂ method or by physical methods such as electrophoration or microinjection into prokaryotic cells such as *E. coli*. There is no specific limitation for the host. For instance *E. coli* strain may be selected form BL21(DE3), BLR(DE3), B834(DE3), AD494(DE3), JM109(DE3), HMS174(DE3), UT400(DE3) and UT5600(DE3). Culture medium could be selected from LB, M9, M9CA, and R according to the characteristics of the host or transformants cells. Growth factors may be added to the media depending on the host requirements.

LB medium (bacto-tryptone 10 g/l, yeast extract 5 g/l, NaCl 10 g/l)

M9 medium (Na₂PO₄ 7H₂O 12.8 g/l, KH₂PO₄ 3.0 g/l, NaCl 0.5 g/l, NH₄Cl 1 g/l, glucose 4 g/l, MgSO₄ 2 mM, CaCl₂ 0.1 mM)

M9CA medium (M9 medium+0.2% casamino acid)

R medium (Reisenberg medium; KH₂PO4 13.3 g/l, (NH₄)₂PO₄ 4.0 g/l, citric acid 0.17 g/l, MgSO₄ 7H₂O 0.22 g/l, glucose 20 g/l, trace element solution 10 ml/l)

Trace element solution (ferric citrate 7.3 g/l, CoCl₂ 6H₂O 0.5 g/l, MnCl₂ 4H₂O 3.2 g/l, CuCl₂ 2H₂O 0.3 g/l, H₃BO₃ 0.7 g/l, NaMoO₄ 2H₂O 1.68 g/l, Thiamin HCl 0.5 g/l, EDTA 1 g/l)

The invention will be further illustrated in detail by the following examples. It will be apparent to those having conventional knowledge in this field that these examples are given only to explain the present invention more clearly, but the invention is not limited to the examples given below.

EXAMPLE 1

Preparation of a Gene Coding for an Antimicrobial Peptide

Two different MSI-344 genes were synthesized by the PCR method to express MSI-344 gene efficiently in *E. coli* and to ease the gene manipulation (FIG. 1). Template for PCR was pNH18a-MBP-MSI-78 described in Korean patent application 97-29426. Sequence (a) (SEQ ID NO. 55) was synthesized using primers No. 1 (SEQ ID NO. 1) and No. 2 (SEQ ID NO. 2) in Table 1 which was designed to separate MSI-344 by CNBr cleavage from the fusion peptide, and Sequence (b) (SEQ ID NO. 57) was synthesized using primers No. 3 (SEQ ID NO. 3) and No. 4 (SEQ ID NO. 4) in Table 1 which was designed to be cleaved by hydroxylamine. To subclone MSI-344 gene with correct reading frame into the expression vector, Nde1 (Sequence (a)) and SmaI (Sequence (b)) sites were inserted in front of MSI-344 gene and stop codons TAA and TGA were inserted behind the MSI-344 gene. Also to construct the transcriptional multimer, a ribosome binding site that overlaps 1 base pair with the stop codon and Ase I site were inserted. These two MSI-344 genes were cloned into pCR2.1 vector (Invitrogen, USA) to prepare vector pCRMSI containing sequence (a) and vector pCRMSI' containing sequence (b).

The antimicrobial peptide genes in FIG. 1 were prepared by annealing chemically synthesized oligonucleotides (Table 1) or by performing PCR after annealing. In the case of Apidaecin I (SEQ ID NO. 41), Indolicidin (SEQ ID NO. 51), and Tachyplesin I (SEQ ID NO. 61), DNA sequence was based on the amino acid sequence of a peptide (Maloy and Kark, Peptide Science, 37: 105, 1995) and the gene was chemically synthesized by using codons that can maximize the expression level in *E. coli*. In the case of Bombinin (SEQ ID NO. 43), CPF1 (SEQ ID NO. 45), Drosocin (SEQ ID NO. 47), Melittin (SEQ ID NO. 53), HNP-I (SEQ ID NO. 49), PGQ (SEQ ID NO. 59), and XPF (SEQ ID NO. 63), the N- and C-terminal oligonucleotides which were designed to anneal to each other by 8–10 bp overlaps, were synthesized and the peptide gene was synthesized by PCR after annealing two oligonucleotides. The characteristics of each antimicrobial peptide are listed in Table 2.

| | Sequences (5' ---> 3') | Primers |
|---|---|---|
| 1 | TCCGGATCCATATGGGTATCGGCAAAT TCCTG (SEQ ID NO. 1) | Primers for the synthesis of MSI-344 (32 mer) |
| 2 | GCATTAATATATCTCCTTCATTACTTTT TCAGGATTTTAACG (SEQ ID NO. 2) | Primers for the synthesis of MSI-344 (42 mer) |
| 3 | GGATCCCGGGATCGGCAAATTCCTGA AAAAGG (SEQ ID NO. 3) | Primers for the synthesis of MSI-344 (32 mer) |
| 4 | GGATCCATTAATATATCTCCTT CATTAC (SEQ ID NO. 4) | Primers for the synthesis of MSI-344 (28 mer) |
| 5 | GGTAACAACCGTCCGGTTTACATCCCG CAGCCGCGTCCGCCGCCACCCGCGTAC TTGA (SEQ ID NO. 5) | Primers for the synthesis of Apidaecin I (57 mer) |
| 6 | AATTCTCAAGTACGCGGGTGCGGCGG ACGCGGCTGCGGGATGTAAACCGGAC GGTTGTTACC (SEQ ID NO. 6) | Primers for the synthesis of Apidaecin I (62 mer) |
| 7 | GGTATCGGTGCGCTGTCTGCGAAAGG TGCGCTGAAAGGTCTGGCGAAA (SEQ ID NO. 7) | Primers for the synthesis of Bombinin (48 mer) |
| 8 | CGAATTCTCAGTTCGCGAAGTGTTGCG CCAGACCTTTCGCCAGACCTTTCAGCG CACC (SEQ ID NO. 8) | Primers for the synthesis of Bombinin (58 mer) |
| 9 | GGTTTCGCGTCTTTCCTGGGTAAAGCG CTGAAAGCGGCGCTGAAAATC (SEQ ID NO 9) | Primers for the synthesis of CPF (48 mer) |
| 10 | CGAATTCTCACTGCTGCGGCGCACCAC CCAGCGCGTTCGCACCGATTTTCAGC GCCGCTT (SEQ ID NO. 10) | Primers for the synthesis of CPF (60 mer) |
| 11 | GGTAAACCGCGTCCGTACTCTCCGCG TCCGACCTCTCAC (SEQ ID NO. 11) | Primers for the synthesis of Drosocin (39 mer) |
| 12 | CGAATTCTCAAACCGCGATCGGACGC GGGTGAGAGGTCGGACGCGGAGA (SEQ ID NO. 12) | Primers for the synthesis of Drosocin (49 mer) |
| 13 | GCATGCCATGGCGTGCTACTGCCGTAT CCCGGCGTGCATCGCGGGTGAACGTC GTTACGG (SEQ ID NO. 13) | Primers for the synthesis of HNP-1 (60 mer) |
| 14 | CGAATTCTCAGCAGCAGAACGCCCAC AGACGACCCTGGTAGATGCAGGTA CCGTAACGAC (SEQ ID NO. 14) | Primers for the synthesis of HNP-1 (60 mer) |
| 15 | CATGATCCTGCCGTGGAAATGGCCGT GGTGGCCGTGGCGTCGTTGAG (SEQ ID NO. 15) | Primers for the synthesis of Indolicidin (47 mer) |
| 16 | AATTCTCAACGACGCCACGGCCACC ACGGCCATTTCCACGGCAGGAT (SEQ ID NO. 16) | Primers for the synthesis of Indolicidin (47 mer) |
| 17 | GGTATCGGTGCGGGTATCGGTGCGGT TCTGAAAGTTCTGACCACCGGTCTGCC GGCGCTG (SEQ ID NO. 17) | Primers for the synthesis of Melittin (48 mer) |
| 18 | CGAATTCTCACTGCTGACGTTTACGTT TGATCCAAGAGATCAGCGCCGGCAGA CCGGT (SEQ ID NO. 18) | Primers for the synthesis of Melittin (58 mer) |
| 19 | GGTGTTCTGTCTAACGTTATCGGTTAC CTGAAAAAACTGGGTACC (SEQ ID NO. 19) | Primers for the synthesis of PGQ (45 mer) |
| 20 | CGAATTCTCACTGTTTCAGAACCGCGT TCAGCGCACCGGTACCCAGTTTTTT CAG (SEQ ID NO. 20) | Primers for the synthesis of PGQ (55 mer) |
| 21 | CATGAAATGGTGCTTCCGTGTTTGCTA CCGTGGTATCTGCTACCGTCGTTGCCG TTGAG (SEQ ID NO. 21) | Primers for the synthesis of Tachyplasin (59 mer) |
| 22 | AATTCTCAACGGCAACGACGGTAGC AGATACCCCGGTAGCAAACACGGAAG CACCATTT (SEQ ID NO. 22) | Primers for the synthesis of Tachyplasin (59 mer) |

-continued

| | Sequences (5' ---> 3') | Primers |
|---|---|---|
| 23 | GGTTGGGCGTCTAAAATCGGTCAGAC CCTGGGTAAAATCGCGAAAGTT (SEQ ID NO. 23) | Primers for the synthesis of XPF (48 mer) |
| 24 | CGAATTCTCATTTCGGCTGGATCAGTT CTTTCAGACCAACTTTCGCGATTTTA CCCAG (SEQ ID NO. 24) | Primers for the synthesis of XPF (58 mer) |
| 25 | GGATCCATATGTGCGGTATTGTCGGTA TCG (SEQ ID NO. 25) | Primers for the synthesis of F (30 mer) |
| 26 | CATATGGCGAGCTTCAAATACATCG (SEQ ID NO. 26) | Primers for the synthesis of F (25 mer) |
| 27 | GGATCCATATGTGCGGTATTGTCGGTA TCG (SEQ ID NO. 27) | Primers for the synthesis of F' (30 mer) |
| 28 | GGATCCAATATTAGCTTCAAATACATC GCTC (SEQ ID NO. 28) | Primers for the synthesis of F' (31 mer) |
| 29 | GGATCCATATGTGCGGTATTGTCGGTA TCG (SEQ ID NO. 29) | Primers for the synthesis of F3 (30 mer) |
| 30 | GGATCCAATATTCGCATGCGCAGCTTC AAATACATCG (SEQ ID NO. 30) | Primers for the synthesis of F3 (HA) (37 mer) |
| 31 | CGGGATCCACATGTGGCGAGCTTCAA ATAC (SEQ ID NO. 31) | Primers for the synthesis of F3 (CB) (30 mer) |
| 32 | GGATCCATATGTGCGGTATTGTCGGTA TCG (SEQ ID NO. 32) | Primers for the synthesis of F4 (30 mer) |
| 33 | GCGGATCCACATGTCGGCTTCCAG (SEQ ID NO. 33) | Primers for the synthesis of F4 (CB) (24 mer) |
| 34 | AATATTGTCGGCTTCCAGCGGGTAG (SEQ ID NO. 34) | Primers for the synthesis of F3 (HA) (25 mer) |
| 35 | CATATGCTTGCTGAAATCAAAGG (SEQ ID NO. 35) | Primers for the synthesis of BF (23 mer) |
| 36 | AATATTGCCAGCACCCTCCTGTCCTCG GTG (SEQ ID NO. 36) | Primers for the synthesis of BF (30 mer) |
| 37 | TTCGCTTGCGCGACCACT (SEQ ID NO. 37) | Primers for purF G49A mutant (18 mer) |
| 38 | TGCGAACGGGTGGAGCCGTTAGACTG (SEQ ID NO. 38) | Primers for purF N102L mutant (26 mer) |
| 39 | GCGGATCCAAGAGACAGGATGAGGAT CGTTTCGC (SEQ ID NO. 39) | Primers for the synthesis of kan$^R$ gene (34 mer) |
| 40 | CGGATATCAAGCTTGGAAATGTTGAA TACTCATACTCTTC (SEQ ID NO. 40) | Primers for the synthesis of kan$^R$ gene (40 mer) |

TABLE 2

| | Amino acid residue | Molecular weight (kDa) | Origin |
|---|---|---|---|
| Apidaecin I | 18 | 2.11 | Insect (*A. mellifera*) |
| Bombinin | 24 | 2.29 | Frog (*B. variegata*) |
| Cecropin A | 36 | 3.89 | Moth (*H. cecropia*) |
| CPF1 | 27 | 2.60 | Frog (*X. Laevis*) |
| Drosocin | 19 | 2.11 | Fly (*D. melanogaster*) |
| HNP1 | 30 | 3.45 | Human (alpha-defensin) |
| Indolicidin | 13 | 1.91 | Cow |
| MSI-344 | 22 | 2.48 | Frog (*X. laevis*) |
| Melittin | 26 | 2.85 | Insect (*H. cecropia*) |
| PGQ | 24 | 2.33 | Frog (*X. laevis*) |
| Tachyplesin I | 17 | 2.27 | Crab (*T. tridentatus*) |
| XPF | 25 | 2.64 | Frog (*X. laevis*) |

EXAMPLE 2

Preparation of Fusion Partner

To use as a fusion partner, purF derivatives shown in FIG. 2 were obtained from the chromosomes of *E. coli* and *Bacillus subtilis* using PCR. The fusion partner F was prepared by CNBr cleavage, and F', F5 and BF by for hydroxylamine cleavage. F3 and F4 were prepared as two different forms; one for CNBr cleavage (F3(CB), F4(CB)), and another for hydroxylamine cleavage (F3(HA), F4(HA), F4a(HA)). Fusion partners F, F', F3(HA), F3(CB), F4(HA), F4a(HA), F4a(CB), F5, BF are indicated in sequences No. 1–9, respectively.

1) purF derivative F (SEQ ID NO. 73)

The derivative is a coding for 61 amino acid from the N-terminus of the *E. coli* purF protein (FIG. 2). Nde I site including start codon Met was inserted at the 5' end, and Nde I site including Met codon that encodes cleavage site for CNBr was inserted at the 3' end.

2) purF derivative F' (SEQ ID NO. 75)

To remove the internal hydroxylamine cleavage site, the $49^{th}$ glycine residue (GGG) was substituted with alanine (GCG, see FIG. 2) by site-directed mutagenesis using primer #36 in Table 1, and Ssp I site containing AAT coding for asparagine was added after alanine codon (number 57) by PCR to form a hydroxylamine cleavage site.

3) purF derivative F3

The $49^{th}$ glycine residue was substituted with alanine as in F'. Asparagine at the 58th residue was substituted with alanine and alanine-asparagine was added after the 59th histidine (F3(HA)) (SEQ ID NO. 77). In case of F3 for CNBr cleavage (F3(CB)) (SEQ ID NO. 79), a DNA sequence that codes for Met and includes BspLU11I site was added after histidine at the 59th residue.

4) PurF derivative F4

This derivative is composed of 159 amino acid residues from the N-terminus of the purF protein. There exists two hydroxylamine sites in wild-type purF protein. To remove these sites, the 102nd asparagine codon (AAC) was substituted with leucine codon (CTC, underlined in Table 2) by site-directed mutagenesis with primer #37 (Table 1) to form F4(HA) (SEQ ID NO. 81). F4a(HA) (SEQ ID NO. 83) was prepared by double substitution of the 49th glycine with alanine and the $102^{nd}$ asparagine with leucine. In the case of F4(HA) and F4a(HA) for hydroxylamine cleavage, the SspI site including asparagine codon was added at the 3' end. In the case of F4a(CB) (SEQ ID NO. 85) for CNBr cleavage, BspLU11 I site including Met codon was added at the 3' end.

5) purF derivative F5 (SEQ ID NO. 87)

This derivative composed of a sequence from the $60^{th}$ methionine to the $148^{th}$ aspartic acid of the purF protein, and Ssp I site was added at the 3' end.

6) purF derivative BF (SEQ ID NO. 89)

BF is a purF derivative of *B. subtilis* and includes 43 amino acid residues and Ssp I site coding for Asn at the 3' end.

EXAMPLE 3

Preparation of DNA Construct Coding for Fused Peptides

Among the peptide genes prepared in Example 1, the genes encoding peptide that contains glycine at the first amino acid were fused to fusion partners for the hydroxylamine cleavage, F4a(HA), F5 and BF. Other peptides (HNP-I, Indolicidin, Tachyplesin) were fused to the fusion partners for the CNBr cleavage, F, F3(CB) and F4a(CB) (Table 3).

Figure 3B:
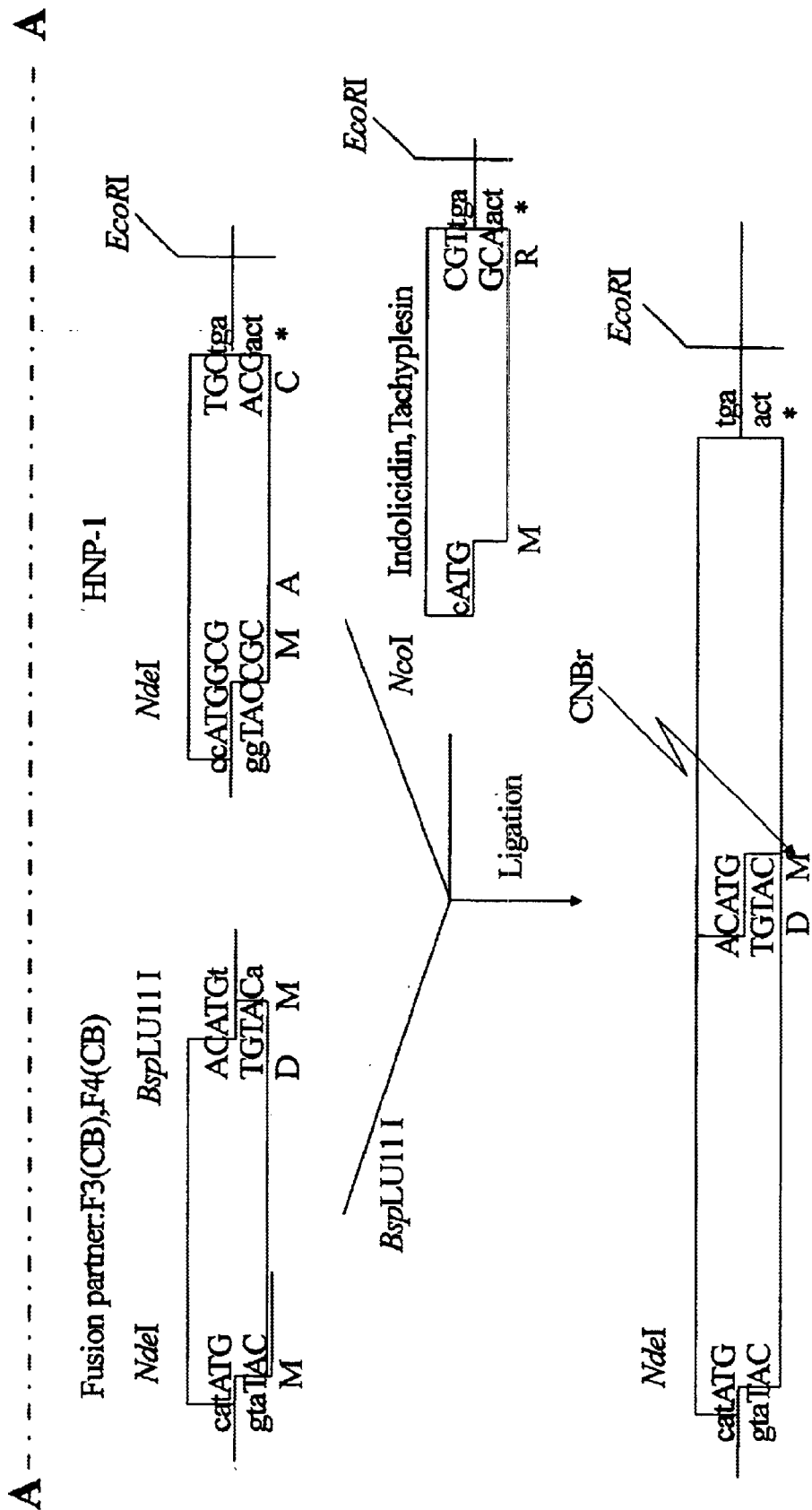
Figure 4A:
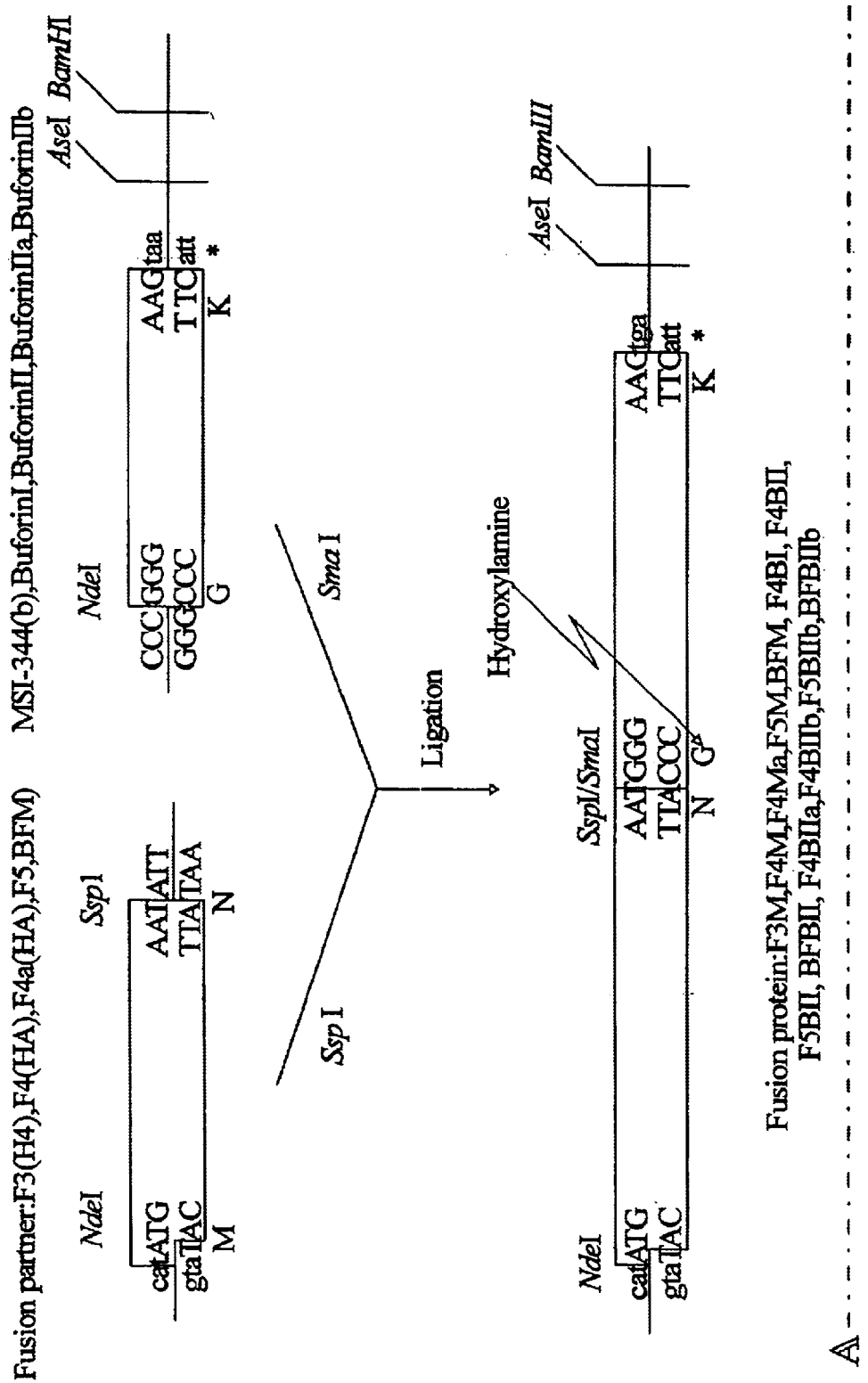
FIGS. 4A and 4B, herein referred to collectively as FIG. 4, are a scheme of a fusion method between the fusion partner and the MSI-344 gene by generating a sequence encoding producing hydroxylamine cleavage site.
Figure 4B:
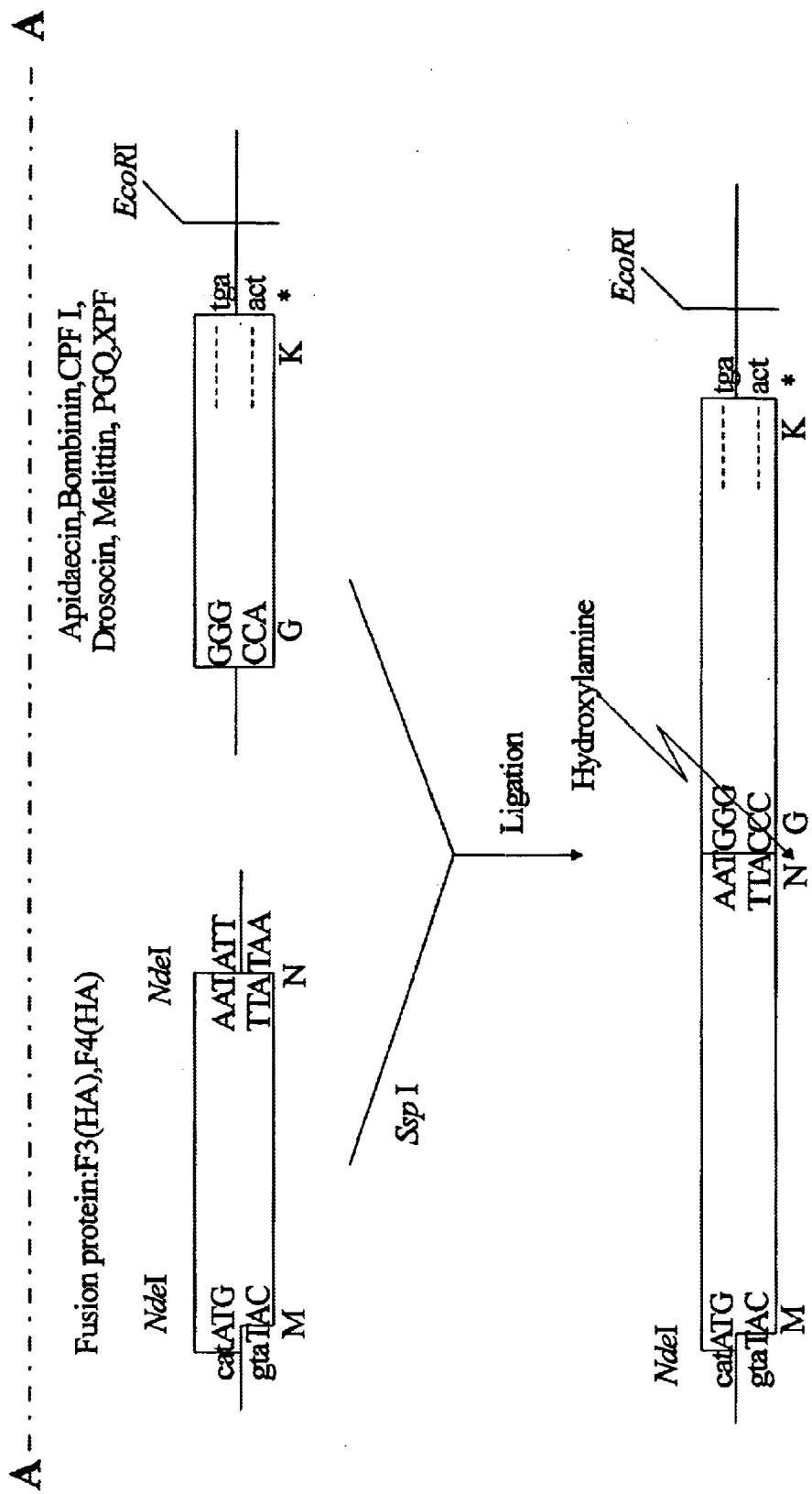
Figure 5:
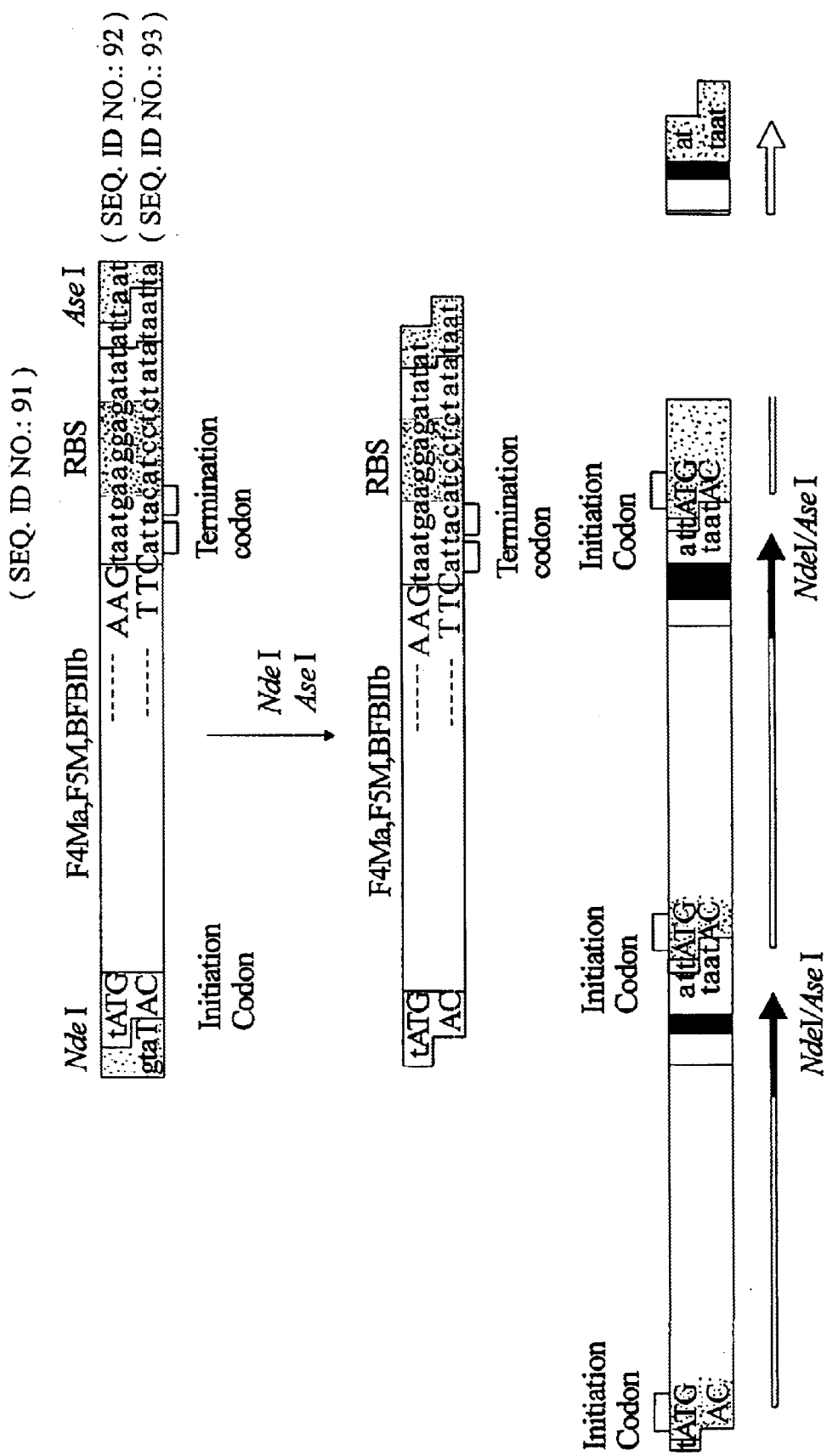
FIG. 5 is a scheme of the construction of the transcriptionally fused multimer.

A method of fusion between the fusion partner and the gene coding for an antimicrobial peptide while producing the CNBr cleavage site (Met) or hydroxylamine cleavage site (Asn-Gly) is shown in FIGS. 3 and 4, respectively. In the case of fusion with fusion partner F for CNBr cleavage, the fusion partner and the MSI-344 gene were fused using the Nde I site to produce DNA construct FM (FIG. 3a). In case of fusion with F3(CB) or F4(CB), the peptide genes are chemically synthesized and fused to 3' end BspLU11 I site of the fusion partner by complementary 5' Nco I site for HNP-I, and 5' BspLu11 I site for indolicidin and tachyplesin, respectively.

The fusion with the fusion partner for hydroxylamine cleavage (F', F3(HA), F4(HA), F4a(HA), F5, BF) was carried out by cleaving the fusion partner with Ssp I and MSI-344 by Sma I, and connecting these DNA fragments to generate Asn-Gly site for the hydroxylamine cleavage. In the case of the genes for Apidaecin I, Bombinin, CPF1, Drosocin, Melittin, PGQ and XPF, it was not necessary to digest with restriction enzyme before the fusion with the fusion partner cleaved with Ssp I, since they have 5' blunt ends.

EXAMPLE 4

Preparation of Transcriptionally Fused Multimer

A monomeric unit that can produce multimers was constructed consisting of Nde I site coding for Met, structural gene, RBS (SEQ ID NO. 91), and Ase I site that connects with Nde I to generate Met. As structural genes, F4a(HA)-MS 1344 fusion gene ( F4Ma ) and F5-MSI344 fusion gene ( F5M ) were used. The monomeric units were digested with Nde I and Ase I, and the isolated monomeric units were reconnected. Obtained DNA fragments were digested again with Nde I and Ase I, and the multimers were separated by agarose gel electrophoreses. By using this method, monomer (F4Ma), dimer (F4MaX2) and tetramer (F4MaX4) of F4Ma and monomer (F5M), dimer (Fm5MX2) and tetramer (F5MX4) of F5M were obtained.

EXAMPLE 5

Expression Vector

Figure 6A:
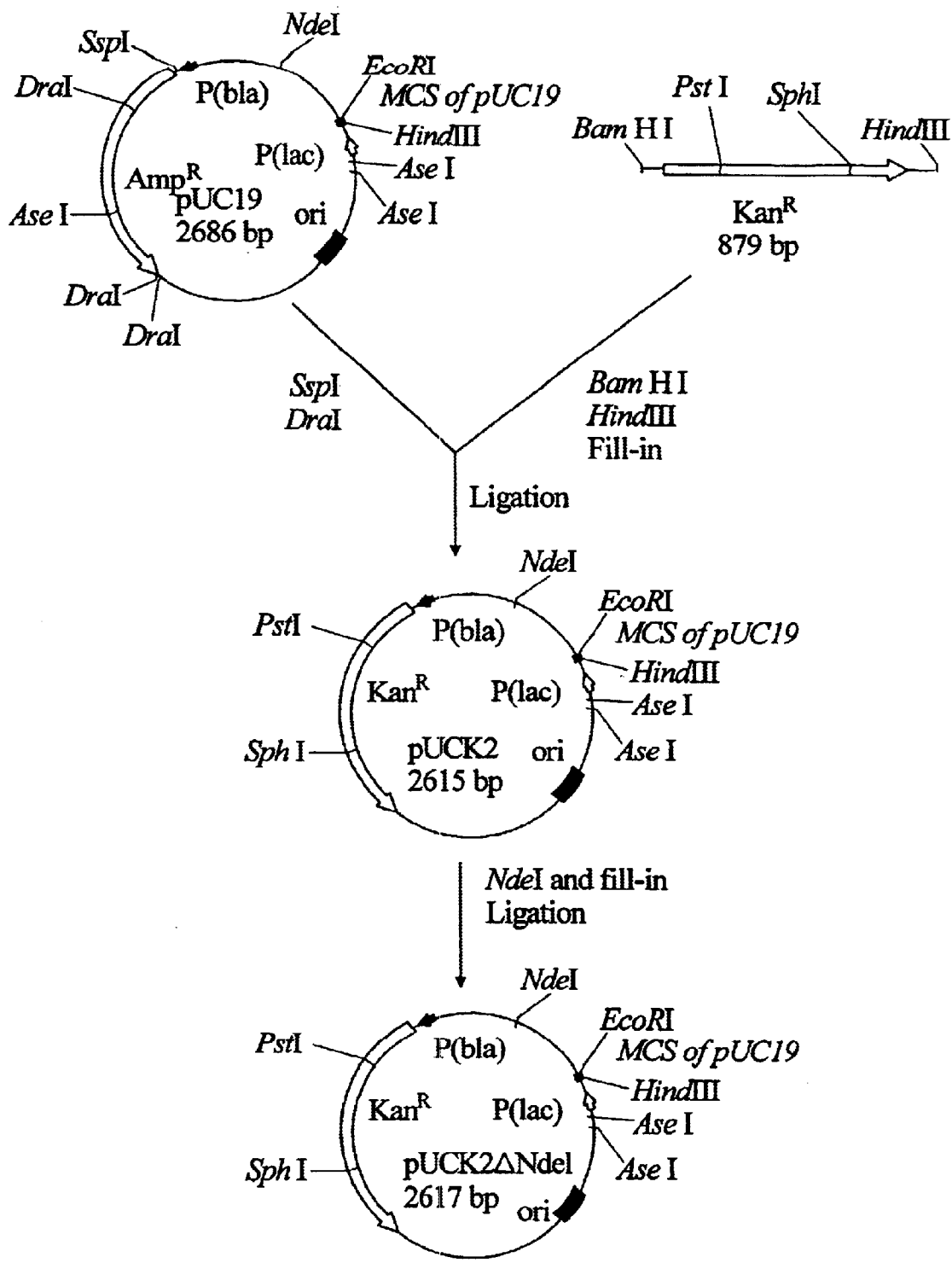

To express foreign gene in *E. coli*, two expression vectors pGNX2 and pT7K2.1 were constructed by using T7Φ10 promoter, high copy number replication origin (colEI of pUC family), and kanamycin resistance gene. To construct pGNX2, bla gene in commercially available pUC19 (ampicillin resistance gene: $Amp^R$) was substituted with kanamycin resistance gene ($Kan^R$). To this end, pUC19 was digested with Ssp I and Dra I to separate 1748 bp DNA fragment having 1748 bp, and $Kan^R$ gene was amplified by PCR by using Tn5 of *E. coli* as a template and primers #39 and #40 (Table 1). The PCR product was digested with BamH I and Hind III, filled-in by Klenow treatment, and cloned int pUC19 digested with Ssp I and Dra I, resulting in pUCK2. After this vector was digested with Nde I and filled in by Klenow treatment, it was religated to contruct pUCK2ΔNdeI. The final plasmid pGNX2 was constructed by cloning the fragment containing T7Φ10 promoter and RBS from pT7-7 (USB, USA) that was digested with BamH I, filled-in by Klenow treatment, and then digested with Ase I, into the pUCK2ΔNdeI vector that was digested with Hind III, filld-in by Klenow treatment, and then digested with Ase I. T7Φ10 promoter and kanamycin resistant gene ($Kan^R$) are oriented to the same direction in pGNX2 (FIG. 6).

Figure 7:
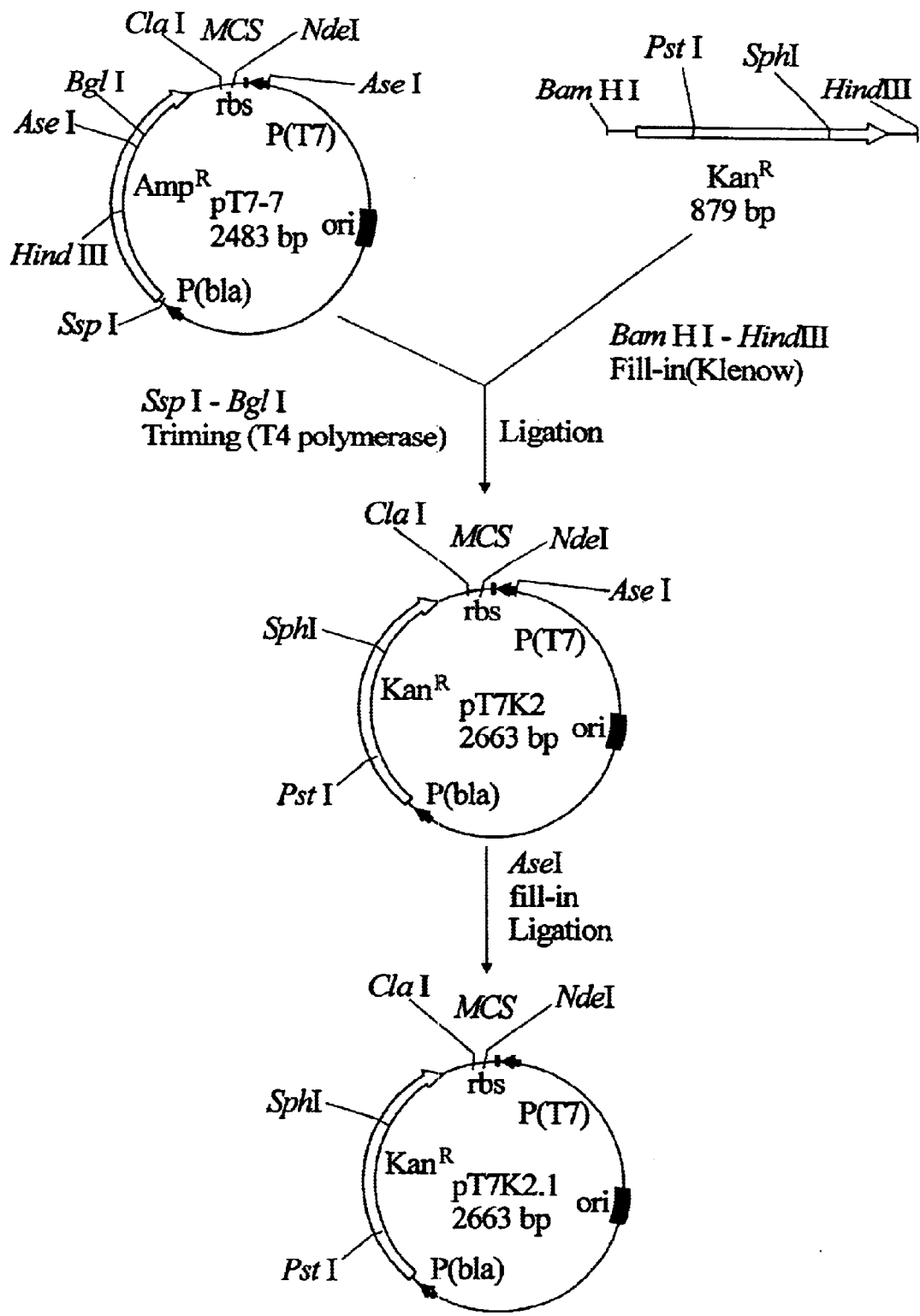
FIG. 7 is a scheme of the construction of the pT7K2.1 vector.
Figure 8:
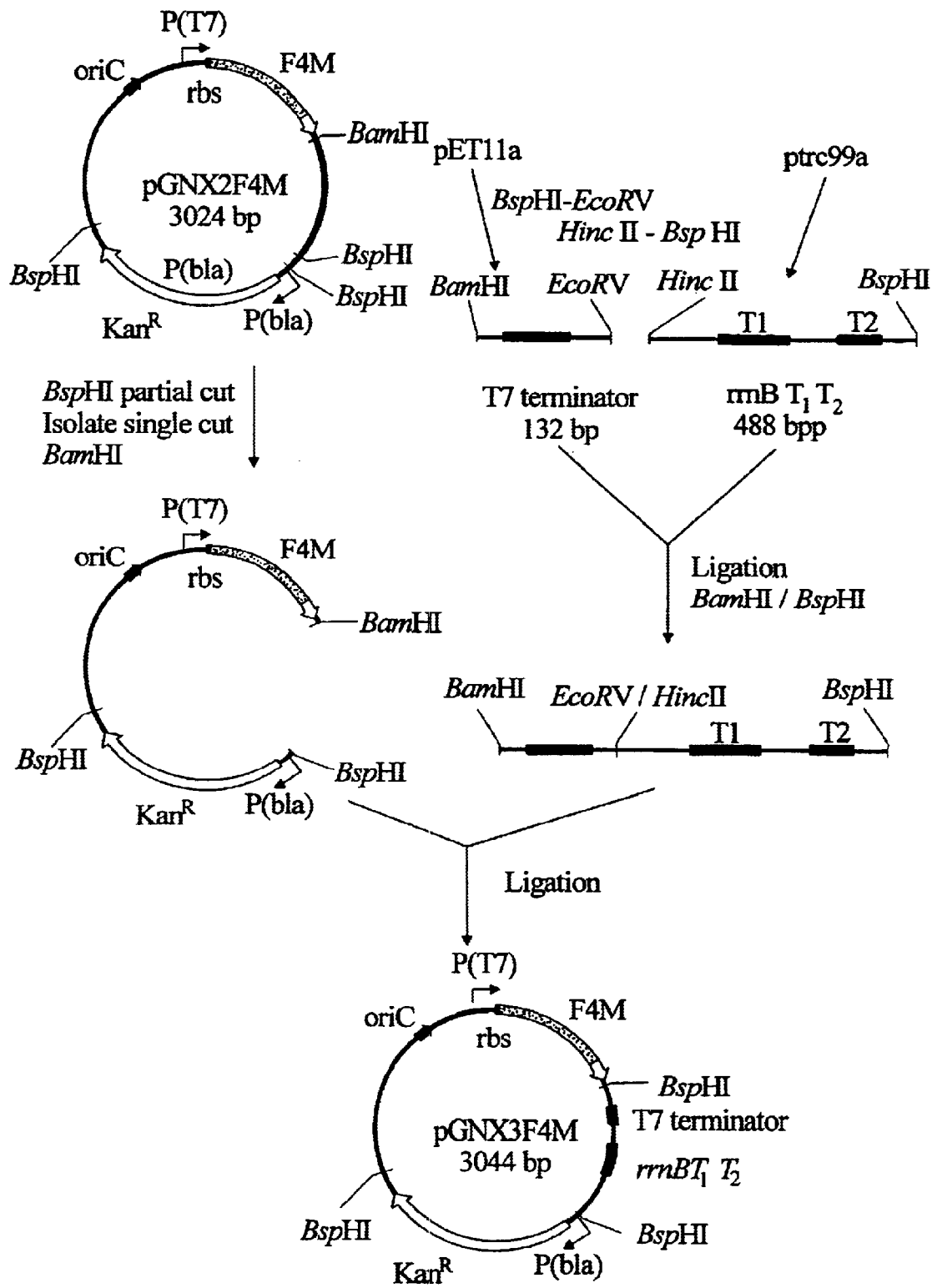
FIG. 8 is a scheme of the construction of the pGNX3 vector.

To construct the plasmid pT7K2.1, the bla gene was removed from pT7-7 by digestion with SspI and Bgl I, and the following treatment with T4 DNA polymerase to make blunt ends. $Kan^R$ gene was prepared as in pGNX2 and the two DNA fragments were ligated to construct pT7K2. Final plasmid pT7K2.1 was constructed by removing Ase I site from this vector (FIG. 7). *E. coli* HMS174 (DE3) transformed with pGNX2 was deposited to Korean Collection of Type Cultures (KCTC) in Korea Research Institute of Bioscience and Biotechnology located at Yusong-gu Eun-dong, Taejon, Korea on May 29, 1998 and the number KCTC0486BP was given. To construct pGNX3, pGNX2F4M was partially digested with BspH I, and the fragment that has a cut in a single BspH I site was separated and further digested with BamH I. To prepare fragment containing T7 and rrnBT1T2 terminators, 132 bp fragment from pET11 a digested with BamH I and EcoR V and a 488 bp fragment from ptrc99a digested with BamH I and EcoR V were ligated. These fused fragments were cleaved by BamH I and BspH I, and cloned into the vector prepared as above to construct pGNX3F4M (FIG. 8).

Figure 9:
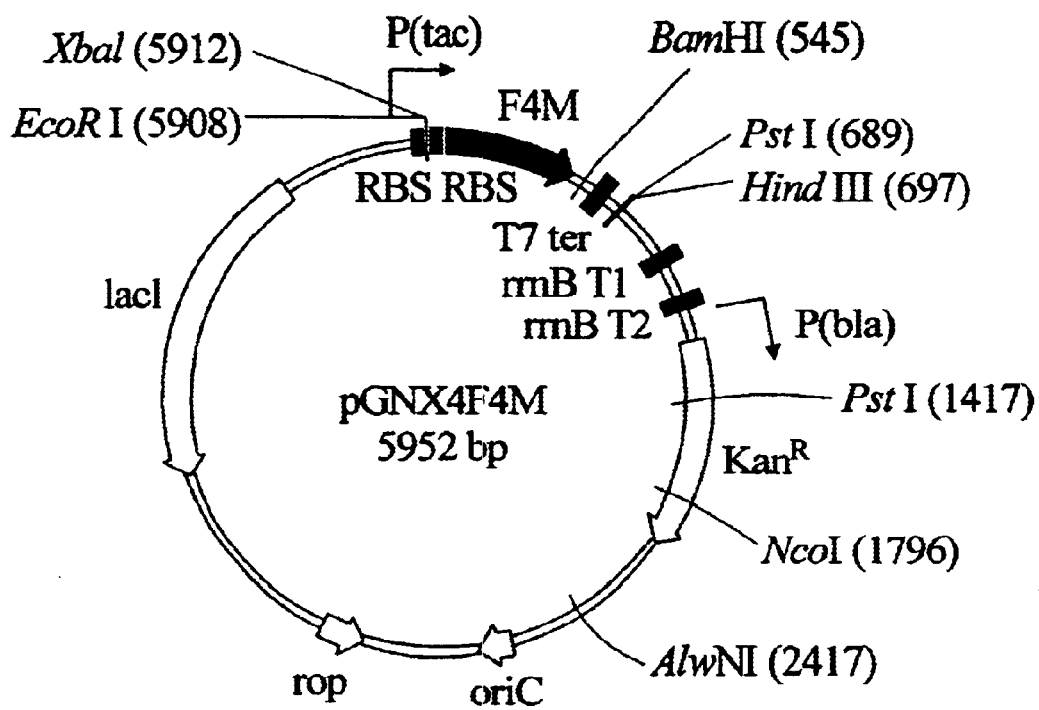
FIG. 9 is the pGNX4 vector.

To prepare pGNX4, a 3052 bp fragment was isolated from pETACc digested with Xba I and AlwN I, and a 2405 bp vector fragment from the pGNX3F4M digested with Xba I and AlwN I resulting in pGNX4F4M (FIG. 9).

Figure 10:
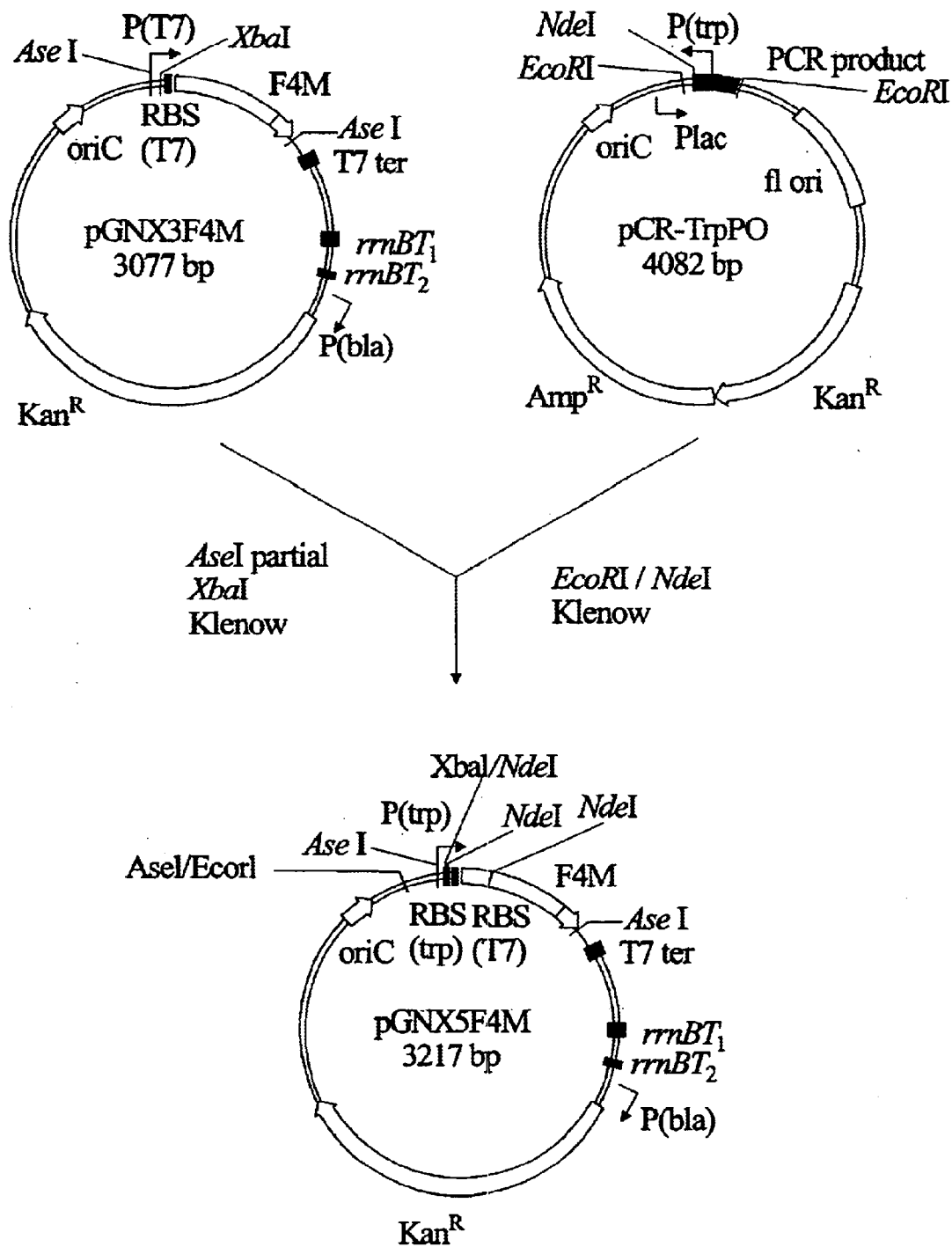
FIG. 10 is a scheme of the construction of the pGNX5 vector.

To construct pGNX5, pGNX3F4M was partially digested with Ase I, then digested with Xba I, and treated with Klenow fragment. A fragment obtained from PCR-TrpPO digested with EcoR I and Nde I and then treated with Klenow fragment was cloned with the above vector fragment to construct pGNX5F4M (FIG. 10).

EXAMPLE 6

Production of Antimicrobial Peptides

DNA constructs obtained by fusing the MSI-344 to fusion partners, F3, F4, F4a, F5 and BF, were cloned into pGNX2 digested with Nde I and BamH I and pT7K2.1 digested with Nde I and BamH I, respectively. In case F (entire purF) was used as the fusion partner, it was cloned into pET24a (Novagen, USA) digested with Nde I and Xho I. In case of a multimer, it was cloned into the Nde I site of pGNX2 and pT7K2.1. The genes coding for Apidaecin I, Indolicidin, Tachyplesin I, Bombinin, CPF1, Drosocin, Melittin, HNP-I, PGQ and XPF were fused to the fusion partner F4 and cloned into pGNX2 digested with Nde I and EcoRI. When F3 was used, BamH I and EcoR I sites of pRSETc were used for cloning (Table 3).

Figure 11:
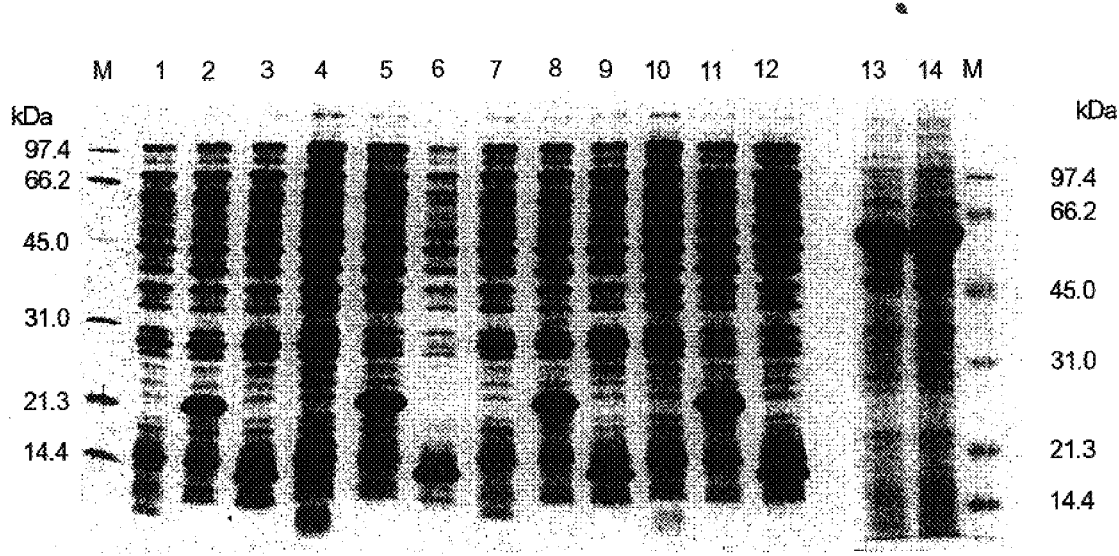
FIG. 11 is a SDS-PAGE electrophoretic analysis of the lysates of the transformants expressing MSI-344 by an induction with lactose or IPTG.
Figure 12:
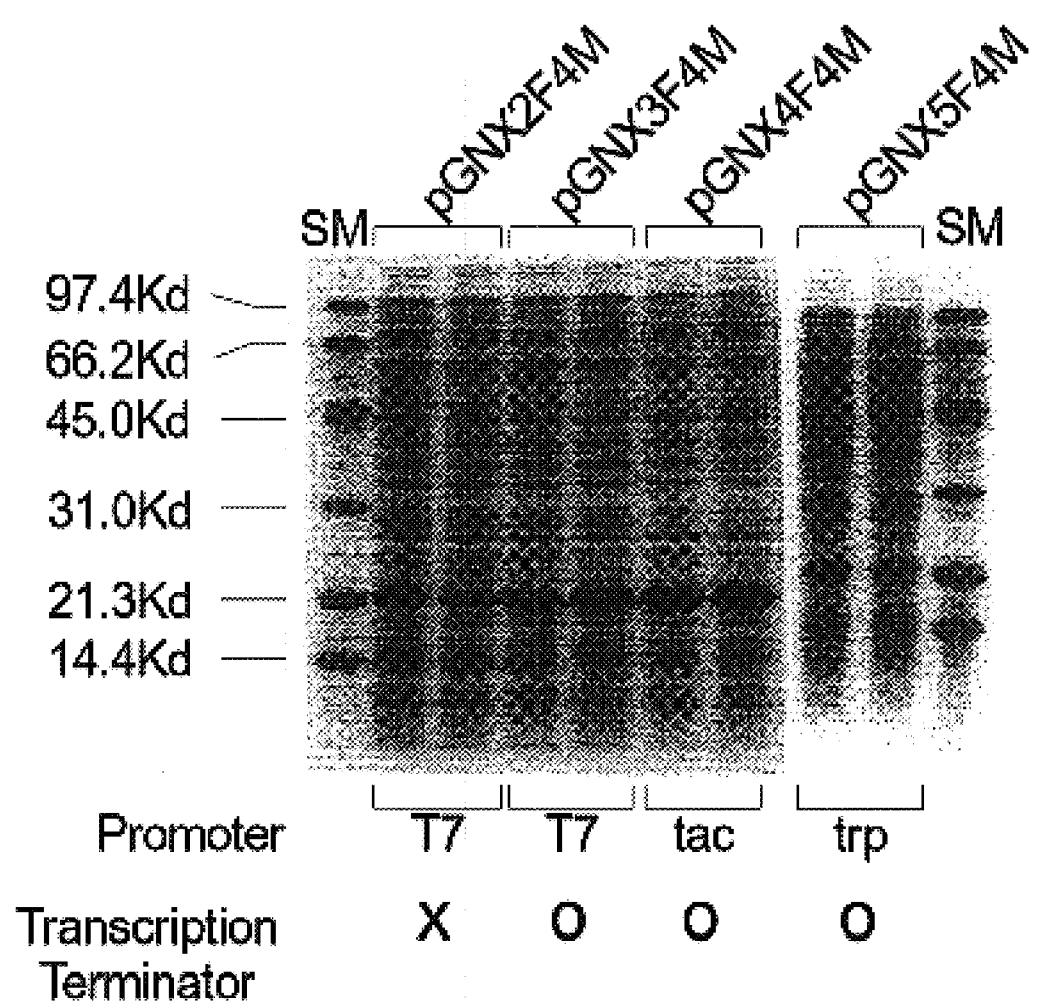
FIG. 12 is a SDS-PAGE electrophoretic analysis of MSI-344 expression with various vectors.

The plasmids 2,3,4,5,6 and 7 in Table 3 were transformed into *E.coli* HMS174(DE3) by using the $CaCl_2$ method. R medium supplemented with casamino acid was used as a culture medium, and the peptide expression was induced when $OD_{600}$ was between 0.2 and 0.4 by adding 2% lactose and 2 mM IPTG, respectively. The expression level was quantified by scanning the results from SDS-PAGE by a densitometer and as the percent of fusion peptide in total cell proteins (FIG. 11). In FIG. 11, M represents molecular weight standard marker, and lanes 1 through 6 represent the expression from the transformants with plasmids 2,3,4,5,6, and 7 in Table 3 by lactose induction, and lanes 7 through 12 represent the expression from the transformants with plasmids 2,3,4,5,6, and 7 in Table 3 by IPTG induction. Lanes 13 and 14 represent the expression from the transformant with plasmid 43 (*E. coli* purF; EF) by lactose and IPTG induction, respectively. As in the same manner, MSI-344 was expressed using *E.coli* HMS174(DE3) transformed with plasmids 44, 45 and 46 in Table 3 and by lactose induction (FIG. 12). It can be seen that the expression level is higher with the plasmid having transcriptional terminator. With the HMS174 (DE3) transformed with plasmid 4 in Table 3, the expression of fusion peptide was induced by lactose and cells were harvested 9 hours after induction. The cells were sonicated and precipitates were obtained by centrifugation. After dissolving the precipitates by placing for 2 hours at room temperature in solution containing 9 M urea, 20 mM potassium phosphate (pH 8.5), the sample was loaded onto SP-sepharose FF column (Pharmacia, Sweden), and the fusion peptide F4Ma was eluted using 0.3~1.0 M NaCl. Purified F4Ma was reacted in 0.5~2 M hydroxylamine and 0.4 M potassium carbonate (pH 7.5~9.5) buffer to cleave MSI-344 from the fusion partner. After desalting, the reaction mixture was loaded onto SP sepharose FF column (Pharmacia, Sweden) again to elute MSI-344 with 0.4~1 M NaCl. Purified MSI-344 was identified by HPLC, MALDI-MS and amino acid sequencing.

EXAMPLE 7

Figure 13A:
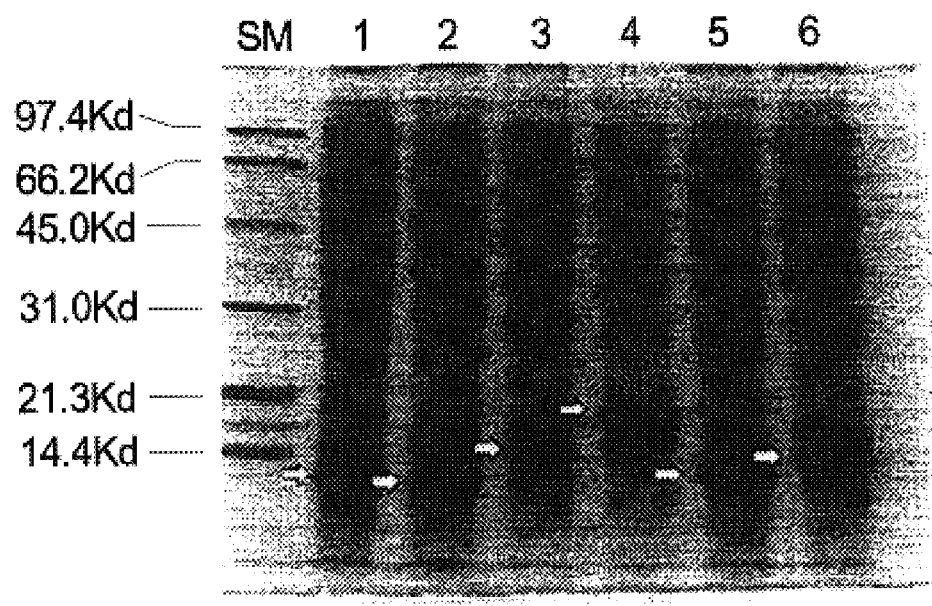
FIG. 13a is a SDS-PAGE electrophoretic analysis of the lysates of the transformants expressing various antimicrobial peptides by induction with lactose.
Figure 13B:
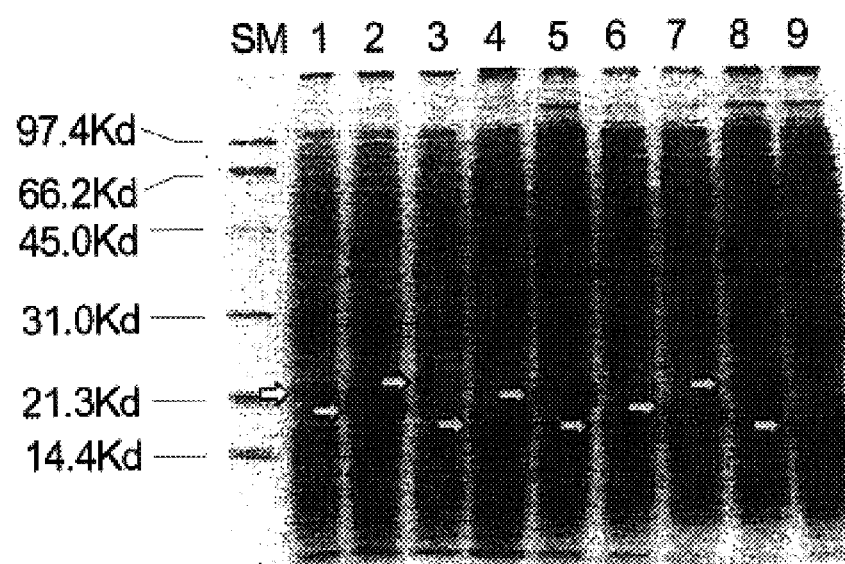
FIG. 13b is a SDS-PAGE electrophoretic analysis of the lysates of the transformants expressing various antimicrobial peptides by an induction with lactose.

Other plasmids in Table 3 were transformed into *E. coli* HMS1 74 (DE3) by $CaCl_2$ method. R medium supplemented with casamino acid was used as a culture medium, and the peptide expression was induced by adding 2% lactose when $OD_{600}$ was between 0.4 and 0.6. The expression level was quantified by scanning the results from SDS-PAGE by a densitometer and as the percent of fusion peptide in total cell proteins. The results of the expression of each antimicrobial peptide are shown in FIGS. 13*a* and 13*b* and Table 3. In FIG. 13*a*, lanes 1 through 6 represent the results from the transformants with plasmids 10,12,15,20,21 and 23 in Table 3. In FIG. 13*b*, lanes 1 through 9 represent the results from the transformants with plasmids 11,13,14,16,22,17,18,24 and 19 in Table 3. FIGS. 14*a*–14*d* represent the expression results of plasmids 25–42 in Table 3. Buforin IIbx2 and Buforin IIx4 are dimer and tetramer of Buforin IIb, respectively, and constructed as described in Example 4. The corresponding plasmids, systems and expression results were indicated in parenthesis below:

| No | peptide | Fusion partner | Cleaving method | Cloning vector | Plasmid | strain | Expression rate (%) |
|---|---|---|---|---|---|---|---|
| 1 | MSI-344 (SEQ ID NO. 55) | F | CNBr | pET24a | PETFM | BL21(DE3) BLR(DE3) | 9 |
| 2 | MSI-344 (SEQ ID NO. 57) | F3 | HA | pGNX2 | pGNX2F3M | BL21(DE3) HMS174(DE3) | 10 |
| 3 | MSI-344 (SEQ ID NO. 57) | F4(HA) | HA | pGNX2 | pGNX2F4M | BL21(DE3) HMS174(DE3) JM109(DE3) UT400(DE3) UT5600(DE3) | 30 |
| 4 | MSI-344 (SEQ ID NO. 57) | F4(HA) | HA | pGNX2 | pGNX2F4Ma | BL21(DE3) HMS174(DE3) JM109(DE3) UT400(DE3) UT5600(DE3) | 30 |
| 5 | MSI-344 (SEQ ID NO. 57) | F4(HA) | HA | pT7K2.1 | pT&KF4M | BL21(DE3) HMS174(DE3) JM109(DE3) UT400(DE3) UT5600(DE3) | 30 |
| 6 | MSI-344 (SEQ ID NO. 57) | F4(HA)a | HA | pT7K2.1 | pT&KF4Ma | BL21(DE3) HMS174(DE3) JM109(DE3) UT400(DE3) UT5600(DE3) | 30 |
| 7 | MSI-344 (SEQ ID NO. 57) | F5 | HA | pGNX2 | pGNX2F5M | BL21(DE3) HMS174(DE3) | 20 |
| 8 | MSI-344 (SEQ ID NO. 57) | F5 | HA | pT7K2.1 | pT7KF5M | BL21(DE3) HMS174(DE3) | 20 |
| 9 | MSI-344 (SEQ ID NO. 57) | BF | HA | pGNX2 | pGNX2BFM | BL21(DE3) HMS174(DE3) | 12 |
| 10 | Apidaecin I (SEQ ID NO. 41) | F3 | HA | pRSETc | pRF2Ap | BL21(DE3) pLysS | 25 |
| 11 | Apidaecin I (SEQ ID NO. 41) | F4(HA) | HA | pGNX2 | pGNX2F4Ap | BL21(DE3) pLysS | 8.7 |
| 12 | Bombinin (SEQ ID NO. 43) | F3 | HA | pRSETc | pRF3Bp | BL21(DE3) pLysS | 23 |
| 13 | Bombinin (SEQ ID NO. 43) | F4(HA) | HA | pGNX2 | pGNX2F4Ap | BL21(DE3) pLysS | 33.6 |
| 14 | CPF (SEQ ID NO. 45) | F4(HA) | HA | pGNX2 | pGNX2F4Cpf | BL21(DE3) pLysS | 9.0 |
| 15 | Drosocin (SEQ ID NO. 47) | F3 | HA | pRSETC | pRF3Dp | BL21(DE3) pLysS | 14 |
| 16 | Drosocin (SEQ ID NO. 47) | F4(HA) | HA | pGNX2 | pGNX2F4Dp | BL21(DE3) pLysS | 25 |
| 17 | Melittin (SEQ ID NO. 53) | F4(HA) | HA | pGNX2 | pGNX2F4Me1 | BL21(DE3) pLysS | 26 |

-continued

| No | peptide | Fusion partner | Cleaving method | Cloning vector | Plasmid | strain | Expression rate (%) |
|----|---------|----------------|-----------------|----------------|---------|--------|---------------------|
| 18 | PGQ (SEQ ID NO. 59) | F4(HA) | HA | pGNX2 | pGNX2F4Pg | BL21(DE3) pLysS | 20.2 |
| 19 | XPF (SEQ ID NO. 63) | F4(HA) | HA | pGNX2 | pGNX2F4Xp | BL21(DE3) pLysS | 26.5 |
| 20 | HNP-I (SEQ ID NO. 49) | F3 | CNBr | pRSETc | pRF3Hp | BL21(DE3) pLysS | 26.3 |
| 21 | Indolicidin (SEQ ID NO. 51) | F3 | CNBr | pRSETc | pRF3Id | B21(DE3) pLysS | 29 |
| 22 | Indolicidin (SEQ ID NO. 51) | F4(CB) | CNBr | pGNX2 | pGNX2F4Id | BL21(DE3) pLysS | 20.7 |
| 23 | Tachyplesin I (SEQ ID NO. 61) | F3 | CNBr | pRSETc | pRF3Tp | BL21(DE3) pLysS | 30 |
| 24 | Tachyplesin I (SEQ ID NO. 61) | F4(CB) | CNBr | pGNX2 | pGNX2F4Tp | BL21(DE3) pLysS | 21.8 |
| 25 | Buforin I (SEQ ID NO. 65) | F4(HA) | HA | pGNX3 | pGNX3F4BI | HMS174(DE3) | 25 |
| 26 | Buforin II (SEQ ID NO. 67) | F4(HA) | HA | pGNX3 | pGNX3F4BII | HMS174(DE3) | 30 |
| 27 | Buforin II (SEQ ID NO. 67) | F5(HA) | HA | pGNX3 | pGNX3F4BII | HMS174(DE3) | 20 |
| 28 | Buforin II (SEQ ID NO. 67) | F5(HA) | HA | pGNX4 | pGNX3F4BII | HMS174(DE3) | 18 |
| 29 | Buforin II (SEQ ID NO. 67) | BF(HA) | HA | pGNX3 | pGNX3F4BII | HMS174(DE3) | 4 |
| 30 | Buforin II (SEQ ID NO. 67) | BF(HA) | HA | pGNX4 | pGNX3F4BII | HMS174(DE3) | 4 |
| 31 | Buforin IIa (SEQ ID NO. 69) | F4(HA) | HA | pGNX3 | pGNX3F4BIIa | HMS174(DE3) | 28 |
| 32 | Buforin IIa (SEQ ID NO. 69) | F5(HA) | HA | pGNX3 | pGNX3F4BIIa | HMS174(DE3) | 20 |
| 33 | Buforin IIa (SEQ ID NO. 69) | F5(HA) | HA | pGNX4 | pGNX3F4BIIa | HMS174(DE3) | 18 |
| 34 | Buforin IIa (SEQ ID NO. 69) | BF(HA) | HA | pGNX3 | pGNX3F4BIIa | HMS174(DE3) | 4 |
| 35 | Buforin IIa (SEQ ID NO. 69) | BF(HA) | HA | pGNX4 | pGNX3F4BIIa | HMS174(DE3) | 4 |
| 36 | Buforin IIb (SEQ iD NO. 71) | F4(HA) | HA | pGNX3 | pGNX3F4BIIb | HMS174(DE3) | 25 |
| 37 | Buforin IIb (SEQ ID NO. 71) | F5(HA) | HA | pGNX3 | pGNX3F4BIIb | HMS174(DE3) | 20 |
| 38 | Buforin IIb (SEQ ID NO. 71) | F5(HA) | HA | pGNX4 | pGNX3F4BIIb | HMS174(DE3) | 18 |
| 39 | Buforin IIb (SEQ ID NO. 71) | BF(HA) | HA | pGNX3 | pGNX3F4BIIb | HMS174(DE3) | 20 |
| 40 | Buforin IIb (SEQ ID NO. 71) | BF(HA) | HA | pGNX4 | pGNX3F4BIIb | HMS174(DE3) | 15 |
| 41 | Buforin IIbx2 (SEQ ID NO. 71) | BF(HA) | HA | pGNX4 | pGNX3F4BIIbx2 | HMS174(DE3) | 20 |
| 42 | Buforin IIbx4 (SEQ ID NO. 57) | BF(HA) | HA | pGNX4 | pGNX3F4BIIbx4 | HMS174(DE3) | 20 |
| 43 | MSI-344 (SEQ ID NO.57) | EF | HA | pGNX2 | pGNX2EFM | HMS174(DE3) | 30 |
| 44 | MSI-344 (SEQ ID NO. 57) | F4(HA) | HA | pGNX3 | pGNX3F4M | HMS174(DE3) | 35 |
| 45 | MSI-344 (SEQ ID NO. 57) | F4(HA) | HA | pGNX4 | pGNX4F4M | HMS174(DE3) | 35 |
| 46 | MSI-344 (SEQ ID NO. 57) | F4(HA) | HA | pGNX5 | pGNX5F4M | HMS174(DE3) | 15 |

EXAMPLE 8

Figure 15:
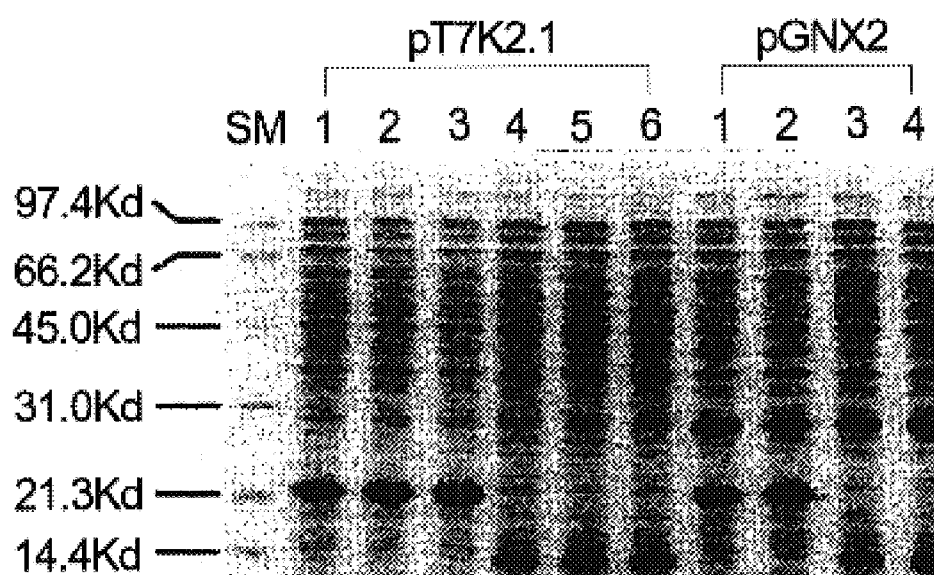
FIG. 15 is a SDS-PAGE electrophoretic analysis of the lysates of the transformants expressing the monomer, dimer and tetramer of the fusion genes.

The constructs prepared in Example 4, such as monomer (F4Ma), dimer (F4MaX2) and tetramer (F4MaX4) of F4Ma and monomer (F5M), dimer (Fm5MX2) and tetramer (F5MX4) of F5M were transformed into E. coli HMS174 (DE3) after cloning them into Nde I site of pGNX2 and at Nde I site of pT7K2.1. Fusion protein was expressed following the method in Example 6, and the expression level was quantified by scanning the results from SDS-PAGE by a densitometer and as the percent of fusion peptide in total cell proteins. In FIG. 15, lanes 1–6 in pT7K2.1 represent F4Ma, F4MaX2, F4MaX4, F5M, F5MX2, and F5MX4, respectively. Lanes 1–4 in pGNX2 represent F4Ma, F4MaX2, F5M and F5MX2, respectively. As can be seen from FIG. 15, the expression level increased from 30% to 40% when the expression of tetramer was compared with that of the monomer. In the case of F5M, the expression level increased from 20% to 25% when the expression of tetramer was compared with that of monomer.

According to the present invention, antimicrobial peptides can be efficiently mass-produced from microorganisms more economically and can be separated and purified easily.

What is claimed is:

1. A DNA construct comprising a first sequence encoding a peptide capable of neutralizing an antimicrobial activity of an antimicrobial peptide, said first sequence comprising a sequence selected from the group consisting of SEQ ID NOS: 73, 75, 77, 79, 81, 83, 85, 87 and 89 and encoding a purF peptide derived from a microorganism or a derivative of the purF peptide, and a second sequence encoding the antimicrobial peptide.

2. A DNA construct according to claim 1 wherein the DNA construct is a multimeric DNA construct composed of repetitive units of 1) a first restriction enzyme site that can generate a methionine initiation codon and a first cohesive end, 2) a DNA construct, 3) a ribosome binding site (RBS), and 4) a second restriction enzyme site which can generate a second cohesive end which can be in-frame fused to the first cohesive end and thus generate the initiation codon.

3. A method for producing an antimicrobial peptide which comprises;
   constructing an expression vector containing a genetic construct, said construct comprising a first sequence coding for a peptide capable of neutralizing an antimicrobial activity of an antimicrobial peptide, said first sequence comprising a sequence selected from the group consisting of SEQ ID NOS: 73, 75, 77, 79, 81, 83, 85, 87 and 89 and encoding a purF peptide derived from a microorganism or a derivative of the purF peptide, and a second sequence encoding the antimicrobial peptide;
   transforming bacterial host cells with said vector;
   culturing the transformed cell to express a peptide as a fusion protein; and
   recovering the fusion protein.

4. A DNA construct according to claim 1, wherein the microorganism is selected from *E. coli* and *B. subtilis*.

5. A DNA construct, comprising;
   a first sequence encoding a peptide capable of neutralizing an antimicrobial activity of an antimicrobial peptide, wherein the first sequence comprises a sequence encoding a peptide selected from the group consisting of SEQ ID NOS: 74, 76, 78, 80, 82, 84, 86, 88, and 90 and encodes a purF peptide derived from a microorganism or a derivative of the purF peptide, and
   a second sequence encoding the antimicrobial peptide.

6. A DNA construct according to claim 1, wherein the antimicrobial peptide comprises a sequence selected from the group consisting of SEQ ID NOS: 42, 44, 46, 48, 50, 52, 54, 56, 58, 60, 62, 64, 66, 68, 70, and 72.

7. A DNA construct according to claim 1, wherein the DNA construct comprises a third sequence between the first and second sequences, the third sequence encoding a cleavage site for a protease or a chemical.

8. A DNA construct according to claim 7, wherein the protease is selected from Factor Xa and enterokinase, and the chemical is selected from CNBr and hydroxylamine.

* * * * *